(12) United States Patent  (10) Patent No.: US 7,901,403 B2
Woloszko et al.  (45) Date of Patent: *Mar. 8, 2011

(54) INTERNALLY LOCATED RETURN ELECTRODE ELECTROSURGICAL APPARATUS, SYSTEM AND METHOD

(75) Inventors: Jean Woloszko, Austin, TX (US);
Thomas Jenkins, Oakland, CA (US);
George Morrison, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 1040 days.

This patent is subject to a terminal disclaimer.

(21) Appl. No.: 11/681,594

(22) Filed: Mar. 2, 2007

(65) Prior Publication Data

US 2007/0208335 A1  Sep. 6, 2007

Related U.S. Application Data

(63) Continuation-in-part of application No. 11/367,254, filed on Mar. 2, 2006.

(51) Int. Cl.
*A61B 18/14* (2006.01)
(52) U.S. Cl. .................... 606/48; 606/41; 606/45
(58) Field of Classification Search .............. 606/46, 606/48–50
See application file for complete search history.

(56) References Cited

U.S. PATENT DOCUMENTS

| | | | |
|---|---|---|---|
| 2,056,377 A | 10/1939 | Wappler | 125/303 |
| 3,633,425 A | 1/1972 | Sanford | 73/356 |
| 3,659,607 A | 5/1972 | Banko | 606/169 |
| 3,815,604 A | 6/1974 | O'Malley et al. | 128/305 |
| 3,828,780 A | 8/1974 | Morrison, Jr. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |

(Continued)

FOREIGN PATENT DOCUMENTS

DE  3930451 A1  3/1991

(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Linda C Dvorak
*Assistant Examiner* — Jaymi Della
(74) *Attorney, Agent, or Firm* — Matthew Scheele; Brian Szymczak

(57) ABSTRACT

A bipolar, plasma-generating electrosurgical apparatus and system wherein the return electrode is enclosed within an electrosurgical shaft, and the active electrode is located on the outside surface of the shaft such that in treating the tissue, the tissue is exposed to plasma generated on the active electrode, but is minimally exposed to electric fields generated between the active and return electrodes. Due to the configuration of the electrodes, electric fields generated between the electrodes are directed away from the target tissue and inwardly towards the return electrode within the shaft, thereby electrical stimulation of neuromuscular structures in the tissue by the electric fields is minimized.

19 Claims, 9 Drawing Sheets

U.S. PATENT DOCUMENTS

| | | | | |
|---|---|---|---|---|
| 4,116,198 | A | 9/1978 | Roos | 128/303 |
| 4,161,950 | A | 7/1979 | Cowan et al. | 606/48 |
| 4,181,131 | A | 1/1980 | Ogiu | 128/303 |
| 4,184,492 | A | 1/1980 | Meinke et al. | 128/303 |
| 4,202,337 | A | 5/1980 | Hren et al. | 128/303 |
| 4,228,800 | A | 10/1980 | Degler, Jr. et al. | 128/303 |
| 4,232,676 | A | 11/1980 | Herczog | 128/303 |
| 4,248,231 | A | 2/1981 | Herczog et al. | 128/303 |
| 4,269,174 | A | 5/1981 | Adair | 128/842 |
| 4,326,529 | A | 4/1982 | Doss et al. | 128/303 |
| 4,381,007 | A | 4/1983 | Doss | 128/303 |
| 4,449,926 | A | 5/1984 | Weiss | 433/32 |
| 4,474,179 | A | 10/1984 | Koch | 606/40 |
| 4,476,862 | A | 10/1984 | Pao | 128/303 |
| 4,483,338 | A | 11/1984 | Bloom et al. | 606/50 |
| 4,532,924 | A | 8/1985 | Auth et al. | 128/303 |
| 4,548,207 | A | 10/1985 | Reimels | 128/303 |
| 4,567,890 | A | 2/1986 | Ohta et al. | 128/303 |
| 4,573,448 | A | 3/1986 | Kambin | 606/170 |
| 4,582,057 | A | 4/1986 | Auth et al. | 606/31 |
| 4,590,934 | A | 5/1986 | Malis et al. | 128/303 |
| 4,593,691 | A | 6/1986 | Lindstrom et al. | 128/303 |
| 4,658,817 | A | 4/1987 | Hardy | 606/14 |
| 4,660,571 | A | 4/1987 | Hess et al. | 128/784 |
| 4,674,499 | A | 6/1987 | Pao | 128/303 |
| 4,682,596 | A | 7/1987 | Bales et al. | 128/303 |
| 4,706,667 | A | 11/1987 | Roos | 128/303 |
| 4,727,874 | A | 3/1988 | Bowers et al. | 128/303 |
| 4,765,331 | A | 8/1988 | Petruzzi et al. | 128/303 |
| 4,785,823 | A | 11/1988 | Eggers et al. | 128/692 |
| 4,805,616 | A | 2/1989 | Pao | 128/303 |
| 4,823,791 | A | 4/1989 | D'Amelio et al. | 123/303 |
| 4,832,048 | A | 5/1989 | Cohen | 128/786 |
| 4,896,671 | A | 1/1990 | Cunningham et al. | 600/374 |
| 4,907,589 | A | 3/1990 | Cosman | 606/34 |
| 4,920,978 | A | 5/1990 | Colvin | 128/784 |
| 4,931,047 | A | 6/1990 | Broadwin et al. | 604/22 |
| 4,936,281 | A | 6/1990 | Stasz | 128/660 |
| 4,936,301 | A | 6/1990 | Rexroth et al. | 606/45 |
| 4,943,290 | A | 7/1990 | Rexroth et al. | 606/45 |
| 4,958,539 | A | 9/1990 | Stasz et al. | 76/104.1 |
| 4,966,597 | A | 10/1990 | Cosman | 606/50 |
| 4,967,765 | A | 11/1990 | Turner et al. | 128/785 |
| 4,976,709 | A | 12/1990 | Sand | 606/5 |
| 4,976,711 | A | 12/1990 | Parins et al. | 606/48 |
| 4,979,948 | A | 12/1990 | Geddes et al. | 606/33 |
| 4,998,933 | A | 3/1991 | Eggers et al. | 606/41 |
| 5,007,908 | A | 4/1991 | Rydell | 606/47 |
| 5,009,656 | A | 4/1991 | Reimels | 606/48 |
| 5,035,696 | A | 7/1991 | Rydell | 606/47 |
| 5,047,026 | A | 9/1991 | Rydell | 606/48 |
| 5,047,027 | A | 9/1991 | Rydell | 606/48 |
| 5,078,717 | A | 1/1992 | Parins et al. | 606/48 |
| 5,080,660 | A | 1/1992 | Buelna | 606/45 |
| 5,084,044 | A | 1/1992 | Quint | 606/27 |
| 5,084,045 | A * | 1/1992 | Helenowski | 606/32 |
| 5,085,659 | A | 2/1992 | Rydell | 606/47 |
| 5,088,997 | A | 2/1992 | Delahuerga et al. | 606/42 |
| 5,098,431 | A | 3/1992 | Rydell | 606/48 |
| 5,099,840 | A | 3/1992 | Goble | 128/422 |
| 5,102,410 | A | 4/1992 | Dressel | 606/15 |
| 5,108,391 | A | 4/1992 | Flachenecker et al. | 606/38 |
| RE33,925 | E | 5/1992 | Bales et al. | 606/48 |
| 5,112,330 | A | 5/1992 | Nishigaki et al. | 606/46 |
| 5,122,138 | A | 6/1992 | Manwaring | 606/46 |
| 5,125,928 | A | 6/1992 | Parins et al. | 606/48 |
| 5,137,530 | A | 8/1992 | Sand | 606/5 |
| 5,156,151 | A | 10/1992 | Imran | 600/375 |
| 5,167,659 | A | 12/1992 | Ohtomo et al. | 606/40 |
| 5,171,311 | A | 12/1992 | Rydell et al. | 606/48 |
| 5,178,620 | A | 1/1993 | Eggers et al. | 606/41 |
| 5,190,517 | A | 3/1993 | Zieve et al. | 604/22 |
| 5,192,280 | A | 3/1993 | Parins | 606/48 |
| 5,195,959 | A | 3/1993 | Smith | 604/34 |
| 5,197,466 | A | 3/1993 | Marchosky et al. | 128/399 |
| 5,197,963 | A | 3/1993 | Parins | 606/46 |
| 5,201,729 | A | 4/1993 | Hertzmann et al. | 606/2 |
| 5,207,675 | A | 5/1993 | Canady | 606/40 |
| 5,207,684 | A | 5/1993 | Nobles | 606/108 |
| 5,217,457 | A | 6/1993 | Delahuerga et al. | 606/42 |
| 5,217,459 | A | 6/1993 | Kamerling | 606/48 |
| 5,230,334 | A | 7/1993 | Klopotek | 601/3 |
| 5,261,410 | A | 11/1993 | Alfano et al. | 600/475 |
| 5,267,994 | A | 12/1993 | Gentelia et al. | 606/15 |
| 5,267,997 | A | 12/1993 | Farin et al. | 606/38 |
| 5,273,524 | A | 12/1993 | Fox et al. | 604/21 |
| 5,277,201 | A | 1/1994 | Stern | 607/98 |
| 5,281,216 | A | 1/1994 | Klicek | 606/42 |
| 5,290,273 | A | 3/1994 | Tan | 606/9 |
| 5,290,282 | A | 3/1994 | Casscells | 606/29 |
| 5,300,069 | A | 4/1994 | Hunsberger et al. | 606/37 |
| 5,306,238 | A | 4/1994 | Fleenor | 606/42 |
| 5,312,400 | A | 5/1994 | Bales et al. | 606/41 |
| 5,314,406 | A | 5/1994 | Arias et al. | 604/21 |
| 5,318,564 | A | 6/1994 | Eggers | 606/47 |
| 5,324,254 | A | 6/1994 | Phillips | 604/21 |
| 5,330,470 | A | 7/1994 | Hagen | 606/42 |
| 5,334,140 | A | 8/1994 | Phillips | 604/35 |
| 5,336,443 | A | 8/1994 | Odashima | 252/511 |
| 5,342,357 | A | 8/1994 | Nardella | 606/40 |
| 5,366,443 | A | 11/1994 | Eggers et al. | 604/114 |
| 5,370,675 | A | 12/1994 | Edwards et al. | 607/101 |
| 5,374,261 | A | 12/1994 | Yoon | 604/385.01 |
| 5,374,265 | A | 12/1994 | Sand | 606/5 |
| 5,375,588 | A | 12/1994 | Yoon | 128/4 |
| 5,380,277 | A | 1/1995 | Phillips | 604/33 |
| 5,380,316 | A | 1/1995 | Aita | 606/7 |
| 5,383,876 | A | 1/1995 | Nardella | 606/49 |
| 5,383,917 | A | 1/1995 | Desai et al. | 607/702 |
| 5,389,096 | A | 2/1995 | Aita | 606/15 |
| 5,395,312 | A | 3/1995 | Desai | 604/22 |
| 5,400,267 | A | 3/1995 | Denen et al. | 702/59 |
| 5,401,272 | A | 3/1995 | Perkins | 606/15 |
| 5,403,311 | A | 4/1995 | Abele et al. | 606/49 |
| 5,417,687 | A | 5/1995 | Nardella et al. | 606/32 |
| 5,419,767 | A | 5/1995 | Eggers et al. | 604/114 |
| 5,423,810 | A | 6/1995 | Goble et al. | 606/40 |
| 5,423,882 | A | 6/1995 | Jackman et al. | 607/122 |
| 5,433,739 | A | 7/1995 | Sluijter et al. | 607/99 |
| 5,436,566 | A | 7/1995 | Thompson et al. | 324/713 |
| 5,437,662 | A | 8/1995 | Nardella | 606/40 |
| 5,438,302 | A | 8/1995 | Goble | 331/167 |
| 5,439,446 | A | 8/1995 | Barry | 604/103 |
| 5,441,499 | A | 8/1995 | Fritzsch | 606/45 |
| 5,451,224 | A | 9/1995 | Goble et al. | 606/48 |
| 5,454,809 | A | 10/1995 | Janssen | 606/41 |
| 5,458,596 | A | 10/1995 | Lax et al. | 606/31 |
| 5,496,312 | A | 3/1996 | Klicek | 606/34 |
| 5,496,314 | A | 3/1996 | Eggers | 606/41 |
| 5,496,317 | A | 3/1996 | Goble et al. | 606/48 |
| 5,514,130 | A | 5/1996 | Baker | 606/41 |
| 5,542,945 | A | 8/1996 | Fritzsch | 606/48 |
| 5,554,152 | A | 9/1996 | Aita | 606/7 |
| 5,556,397 | A | 9/1996 | Long et al. | 606/48 |
| 5,562,703 | A | 10/1996 | Desai | 606/210 |
| 5,569,242 | A | 10/1996 | Lax et al. | 606/42 |
| 5,571,100 | A | 11/1996 | Goble et al. | 606/41 |
| 5,571,189 | A | 11/1996 | Kuslich | 623/17.12 |
| 5,584,872 | A | 12/1996 | LaFontaine et al. | 607/117 |
| 5,609,151 | A | 3/1997 | Mulier et al. | 128/642 |
| 5,617,854 | A | 4/1997 | Munsif | 600/374 |
| 5,626,136 | A | 5/1997 | Webster, Jr. | 600/373 |
| 5,626,576 | A | 5/1997 | Janssen | 606/41 |
| 5,633,578 | A | 5/1997 | Eggers et al. | 323/301 |
| 5,647,869 | A | 7/1997 | Goble et al. | 606/37 |
| 5,660,836 | A | 8/1997 | Knowlton | 424/400 |
| 5,662,680 | A | 9/1997 | Desai | 606/210 |
| 5,676,693 | A | 10/1997 | LaFontaine | 607/116 |
| 5,681,282 | A | 10/1997 | Eggers et al. | 604/114 |
| 5,683,366 | A | 11/1997 | Eggers et al. | 604/114 |
| 5,697,281 | A | 12/1997 | Eggers et al. | 604/114 |
| 5,697,536 | A | 12/1997 | Eggers et al. | 604/114 |
| 5,697,882 | A | 12/1997 | Eggers et al. | 604/114 |
| 5,697,909 | A | 12/1997 | Eggers et al. | 604/114 |
| 5,700,262 | A | 12/1997 | Acosta et al. | 606/48 |
| 5,720,744 | A | 2/1998 | Eggleston et al. | 606/40 |
| 5,725,524 | A | 3/1998 | Mulier et al. | 606/41 |

| | | | | | | | |
|---|---|---|---|---|---|---|---|
| 5,762,629 | A | 6/1998 | Kambin ............... 604/164.11 | 6,228,081 | B1 | 5/2001 | Goble ............................ 606/34 |
| 5,766,153 | A | 6/1998 | Eggers et al. ................ 604/114 | 6,234,178 | B1 | 5/2001 | Goble et al. ................... 606/32 |
| 5,766,252 | A | 6/1998 | Henry et al. ............... 623/17.16 | 6,235,020 | B1 | 5/2001 | Cheng et al. ................... 606/34 |
| 5,785,705 | A | 7/1998 | Baker ............................ 606/32 | 6,237,604 | B1 | 5/2001 | Burnside et al. ............. 128/897 |
| 5,807,306 | A | 9/1998 | Shapland et al. ............... 604/21 | 6,238,391 | B1 | 5/2001 | Olsen et al. ................... 606/41 |
| 5,807,395 | A | 9/1998 | Mulier et al. ................ 606/41 | 6,245,107 | B1 | 6/2001 | Ferree ............................ 606/61 |
| 5,810,764 | A | 9/1998 | Eggers et al. ................ 604/23 | 6,254,600 | B1 | 7/2001 | Willink et al. ................ 606/41 |
| 5,810,809 | A | 9/1998 | Rydell ............................ 606/49 | 6,258,086 | B1 | 7/2001 | Ashley et al. ................ 606/41 |
| 5,820,580 | A | 10/1998 | Edwards et al. ................ 604/22 | 6,261,286 | B1 | 7/2001 | Goble et al. ................... 606/34 |
| 5,823,955 | A | 10/1998 | Kuck et al. ................... 600/374 | 6,261,311 | B1 | 7/2001 | Sharkey et al. ................ 607/96 |
| 5,836,875 | A | 11/1998 | Webster, Jr. ................ 600/374 | 6,264,650 | B1 | 7/2001 | Hovda et al. ................... 606/32 |
| 5,843,019 | A | 12/1998 | Eggers et al. ................ 604/22 | 6,264,651 | B1 | 7/2001 | Underwood et al. ............ 606/32 |
| 5,846,196 | A | 12/1998 | Siekmeyer et al. ........... 600/374 | 6,264,652 | B1 | 7/2001 | Eggers et al. ................ 606/41 |
| 5,849,009 | A | 12/1998 | Bernaz ............................ 606/36 | 6,270,460 | B1 | 8/2001 | McCartan et al. ............. 600/459 |
| 5,860,951 | A | 1/1999 | Eggers ............................ 604/510 | 6,277,112 | B1 | 8/2001 | Underwood et al. ............ 606/32 |
| 5,860,974 | A | 1/1999 | Abele ............................ 606/41 | 6,280,441 | B1 | 8/2001 | Ryan ............................ 606/45 |
| 5,860,975 | A | 1/1999 | Goble et al. ................... 606/45 | 6,283,961 | B1 | 9/2001 | Underwood et al. ............ 606/41 |
| 5,871,469 | A | 2/1999 | Eggers et al. ................ 604/114 | 6,293,942 | B1 | 9/2001 | Goble et al. ................... 606/38 |
| 5,873,855 | A | 2/1999 | Eggers et al. ................ 604/114 | 6,296,636 | B1 | 10/2001 | Cheng et al. ................... 606/32 |
| 5,877,289 | A | 3/1999 | Thorpe et al. ............... 530/387.7 | 6,296,638 | B1 | 10/2001 | Davison et al. ................ 606/41 |
| 5,885,277 | A | 3/1999 | Korth ............................ 606/35 | 6,306,134 | B1 | 10/2001 | Goble et al. ................... 606/42 |
| 5,888,198 | A | 3/1999 | Eggers et al. ................ 604/114 | 6,308,089 | B1 | 10/2001 | von der Rur et al. ......... 600/338 |
| 5,891,095 | A | 4/1999 | Eggers et al. ................ 604/114 | 6,309,387 | B1 | 10/2001 | Eggers et al. ................ 606/41 |
| 5,891,134 | A | 4/1999 | Goble et al. ................... 606/27 | 6,312,408 | B1 | 11/2001 | Eggers et al. ................ 604/114 |
| 5,897,553 | A | 4/1999 | Mulier ............................ 606/41 | 6,319,250 | B1 | 11/2001 | Falwell et al. ................ 606/41 |
| 5,902,272 | A | 5/1999 | Eggers et al. ................ 604/114 | 6,322,549 | B1 | 11/2001 | Eggers et al. ................ 604/500 |
| 5,916,214 | A | 6/1999 | Cosio et al. ................... 606/41 | 6,330,478 | B1 | 12/2001 | Lee et al. ................... 607/101 |
| 5,925,042 | A | 7/1999 | Gough et al. ................... 606/41 | 6,355,032 | B1 | 3/2002 | Hovda et al. ................... 606/32 |
| 5,941,869 | A | 8/1999 | Patterson et al. ............. 604/508 | 6,363,937 | B1 | 4/2002 | Hovda et al. ................. 128/898 |
| 5,944,715 | A | 8/1999 | Goble et al. ................... 606/41 | 6,364,877 | B1 | 4/2002 | Goble et al. ................... 606/34 |
| 5,954,716 | A | 9/1999 | Sharkey et al. ................ 606/32 | 6,379,350 | B1 * | 4/2002 | Sharkey et al. ................ 606/41 |
| 5,980,504 | A | 11/1999 | Sharkey et al. ............... 604/510 | 6,379,351 | B1 | 4/2002 | Thapliyal et al. ............. 606/41 |
| 6,004,319 | A | 12/1999 | Goble et al. ................... 606/48 | 6,391,025 | B1 | 5/2002 | Weinstein et al. ............. 606/41 |
| 6,007,570 | A | 12/1999 | Sharkey et al. ................ 607/96 | 6,402,740 | B1 | 6/2002 | Ellis et al. ...................... 606/28 |
| 6,013,076 | A | 1/2000 | Goble et al. ................... 606/41 | 6,416,507 | B1 | 7/2002 | Eggers et al. ................ 606/32 |
| 6,014,584 | A | 1/2000 | Hofmann et al. ............. 604/21 | 6,416,508 | B1 | 7/2002 | Eggers et al. ................ 606/32 |
| 6,015,406 | A | 1/2000 | Goble et al. ................... 606/41 | 6,416,509 | B1 | 7/2002 | Goble et al. ................... 606/37 |
| 6,024,733 | A | 2/2000 | Eggers et al. ................ 604/500 | 6,428,576 | B1 | 8/2002 | Haldimann ................ 623/17.16 |
| 6,027,501 | A | 2/2000 | Goble et al. ................... 604/114 | 6,432,103 | B1 | 8/2002 | Ellsberry et al. ................ 606/41 |
| 6,036,681 | A | 3/2000 | Hooven ........................ 604/506 | 6,443,988 | B2 | 9/2002 | Felt et al. ................. 623/17.12 |
| 6,039,734 | A | 3/2000 | Goble et al. ................... 606/41 | 6,461,357 | B1 * | 10/2002 | Sharkey et al. ................ 606/45 |
| 6,045,532 | A | 4/2000 | Eggers et al. ................ 604/114 | 6,464,695 | B2 | 10/2002 | Hovda et al. ................... 606/32 |
| 6,047,700 | A | 4/2000 | Eggers et al. ................ 128/898 | 6,468,270 | B1 | 10/2002 | Hovda et al. ................... 606/32 |
| 6,056,746 | A | 5/2000 | Goble et al. ................... 606/48 | 6,468,274 | B1 | 10/2002 | Alleyne et al. ................ 606/32 |
| 6,063,079 | A | 5/2000 | Hovda et al. ................... 606/41 | 6,468,275 | B1 | 10/2002 | Wampler et al. ................ 606/48 |
| 6,066,134 | A | 5/2000 | Eggers et al. ................ 606/32 | 6,482,201 | B1 | 11/2002 | Olsen et al. ................... 606/41 |
| 6,068,628 | A | 5/2000 | Fanton et al. ................ 606/41 | 6,497,704 | B2 | 12/2002 | Ein-Gal ............................ 606/41 |
| 6,073,051 | A | 6/2000 | Sharkey et al. ................ 607/99 | 6,500,173 | B2 | 12/2002 | Underwood et al. ............ 606/32 |
| 6,074,386 | A | 6/2000 | Goble et al. ................... 606/34 | 6,508,839 | B1 | 1/2003 | Lambrecht et al. ........... 623/17.16 |
| 6,086,584 | A | 7/2000 | Miller ............................ 606/41 | 6,517,498 | B1 | 2/2003 | Burbank et al. ................ 600/564 |
| 6,090,106 | A | 7/2000 | Goble et al. ................... 606/41 | 6,530,922 | B2 | 3/2003 | Cosman ............................ 606/34 |
| 6,093,186 | A | 7/2000 | Goble ............................ 606/34 | 6,540,741 | B1 | 4/2003 | Underwood et al. ............ 606/32 |
| 6,093,187 | A | 7/2000 | Lecuyer ............................ 606/80 | 6,558,390 | B2 | 5/2003 | Cragg ............................ 606/80 |
| 6,095,149 | A | 8/2000 | Sharkey et al. ............... 128/898 | 6,562,033 | B2 | 5/2003 | Shah et al. ................... 606/41 |
| 6,096,036 | A | 8/2000 | Bowe et al. ................... 606/41 | 6,575,968 | B1 | 6/2003 | Eggers et al. ................ 606/41 |
| 6,102,046 | A | 8/2000 | Weinstein et al. ............. 128/898 | 6,578,579 | B2 | 6/2003 | Burnside ...................... 128/897 |
| 6,105,581 | A | 8/2000 | Eggers et al. ................ 128/898 | 6,589,237 | B2 | 7/2003 | Woloszko et al. ............. 606/41 |
| 6,109,268 | A | 8/2000 | Thapliyal et al. ............. 128/898 | 6,602,248 | B2 | 8/2003 | Sharps et al. ................ 606/32 |
| 6,117,109 | A | 9/2000 | Eggers et al. ................ 604/114 | 6,604,003 | B2 | 8/2003 | Fredricks et al. ................ 607/99 |
| 6,122,549 | A | 9/2000 | Sharkey et al. ................ 607/99 | 6,620,155 | B2 | 9/2003 | Underwood et al. ............ 606/32 |
| 6,126,682 | A | 10/2000 | Sharkey et al. ................ 607/96 | 6,620,156 | B1 | 9/2003 | Garito et al. ................... 606/50 |
| 6,142,992 | A | 11/2000 | Cheng et al. ................... 606/34 | 6,622,731 | B2 | 9/2003 | Daniel et al. ................. 128/898 |
| 6,146,380 | A | 11/2000 | Racz et al. ................... 606/41 | 6,632,193 | B1 | 10/2003 | Davison et al. ................ 604/22 |
| 6,149,620 | A | 11/2000 | Baker et al. ................... 604/22 | 6,632,220 | B1 | 10/2003 | Eggers et al. ................ 606/41 |
| 6,159,194 | A | 12/2000 | Eggers et al. ................ 604/500 | 6,635,034 | B1 * | 10/2003 | Cosmescu ................... 604/289 |
| 6,159,208 | A | 12/2000 | Hovda et al. ................... 606/41 | 6,635,087 | B2 | 10/2003 | Angelucci et al. ......... 623/17.11 |
| 6,168,593 | B1 | 1/2001 | Sharkey et al. ................ 606/34 | 6,645,247 | B2 | 11/2003 | Ferree ......................... 623/17.11 |
| 6,174,309 | B1 | 1/2001 | Wrublewski et al. ............ 606/45 | 6,679,886 | B2 | 1/2004 | Weikel et al. ................ 606/79 |
| 6,176,857 | B1 | 1/2001 | Ashley ............................ 606/32 | 6,699,244 | B2 * | 3/2004 | Carranza et al. ................ 606/41 |
| 6,179,824 | B1 | 1/2001 | Eggers et al. ................ 604/500 | 6,712,811 | B2 | 3/2004 | Underwood et al. ............ 606/32 |
| 6,179,836 | B1 | 1/2001 | Eggers et al. ................ 606/45 | 6,726,684 | B1 | 4/2004 | Woloszko et al. ............. 606/32 |
| 6,183,469 | B1 | 2/2001 | Thapliyal et al. ............. 606/41 | 6,740,093 | B2 | 5/2004 | Hochschuler et al. .......... 606/94 |
| 6,187,048 | B1 | 2/2001 | Milner et al. ................. 623/17.12 | 6,746,451 | B2 | 6/2004 | Middleton et al. .............. 606/79 |
| 6,190,381 | B1 | 2/2001 | Olsen et al. ................... 606/32 | 6,749,604 | B1 | 6/2004 | Eggers et al. ................ 606/41 |
| 6,203,542 | B1 | 3/2001 | Ellsberry et al. ................ 606/41 | 6,749,605 | B2 | 6/2004 | Ashley et al. ................ 606/41 |
| 6,210,402 | B1 | 4/2001 | Olsen et al. ................... 606/32 | 6,749,608 | B2 | 6/2004 | Garito et al. ................... 606/45 |
| 6,214,001 | B1 | 4/2001 | Casscells et al. ................ 606/41 | 6,758,846 | B2 | 7/2004 | Goble et al. ................... 606/41 |
| 6,224,592 | B1 | 5/2001 | Eggers et al. ................ 606/32 | 6,761,718 | B2 | 7/2004 | Madsen ........................ 606/50 |
| 6,228,078 | B1 | 5/2001 | Eggers ............................ 606/32 | 6,770,071 | B2 | 8/2004 | Woloszko et al. ............. 606/41 |

| | | | |
|---|---|---|---|
| 6,772,012 B2 | 8/2004 | Ricart et al. | 607/99 |
| 6,780,178 B2 | 8/2004 | Palanker et al. | 600/41 |
| 6,780,180 B1 | 8/2004 | Goble et al. | 606/41 |
| 6,802,842 B2 | 10/2004 | Ellman et al. | 606/45 |
| 6,827,716 B2 | 12/2004 | Ryan et al. | 606/41 |
| 6,837,884 B2 | 1/2005 | Woloszko | 606/32 |
| 6,837,887 B2 | 1/2005 | Woloszko et al. | 606/41 |
| 6,837,888 B2 | 1/2005 | Ciarrocca et al. | 606/41 |
| 6,878,155 B2 | 4/2005 | Sharkey et al. | 607/96 |
| 6,920,883 B2 | 7/2005 | Bessette et al. | 128/898 |
| 6,921,399 B2 | 7/2005 | Carmel et al. | 606/41 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,974,480 B2 | 12/2005 | Messerli et al. | 623/17.11 |
| 6,984,231 B2 | 1/2006 | Goble et al. | 606/37 |
| 6,991,631 B2 | 1/2006 | Woloszko et al. | 606/41 |
| 6,997,885 B2 | 2/2006 | Lubock et al. | 600/567 |
| 6,997,925 B2 | 2/2006 | Maguire et al. | 606/41 |
| 7,001,431 B2 | 2/2006 | Bao et al. | 623/17.12 |
| 7,004,941 B2 | 2/2006 | Tvinnereim et al. | 606/41 |
| 7,014,633 B2 | 3/2006 | Cragg | 604/500 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,104,989 B2 | 9/2006 | Skarda | 606/41 |
| 7,108,696 B2 | 9/2006 | Daniel et al. | 606/41 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,276,063 B2 | 10/2007 | Davison et al. | 606/45 |
| 7,297,143 B2 | 11/2007 | Woloszko et al. | 606/41 |
| 7,297,145 B2 | 11/2007 | Ormsby et al. | 606/41 |
| 7,318,823 B2 | 1/2008 | Sharps et al. | 606/32 |
| 7,331,956 B2 | 2/2008 | Hovda et al. | 606/32 |
| RE40,156 E | 3/2008 | Sharps et al. | 606/32 |
| 7,357,798 B2 | 4/2008 | Sharps et al. | 606/32 |
| 7,387,625 B2 | 6/2008 | Hovda et al. | 606/32 |
| 7,393,351 B2 | 7/2008 | Woloszko et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,572,251 B1 | 8/2009 | Davison et al. | 604/500 |
| 7,632,267 B2 | 12/2009 | Dahla | 606/41 |
| 7,691,101 B2 | 4/2010 | Davison et al. | 606/41 |
| 7,704,249 B2 | 4/2010 | Woloszko et al. | 606/48 |
| 7,708,733 B2 | 5/2010 | Sanders et al. | 606/41 |
| 7,824,398 B2 | 11/2010 | Woloszko et al. | 606/41 |
| 2002/0029036 A1 | 3/2002 | Goble et al. | 606/38 |
| 2002/0049438 A1 | 4/2002 | Sharkey et al. | 606/41 |
| 2002/0082698 A1 | 6/2002 | Parenteau et al. | 623/17.16 |
| 2002/0095151 A1 | 7/2002 | Dahla et al. | 606/41 |
| 2002/0120259 A1 | 8/2002 | Lettice et al. | 606/32 |
| 2002/0120337 A1 | 8/2002 | Cauthen | 623/17.16 |
| 2003/0013986 A1 | 1/2003 | Saadat | 600/549 |
| 2003/0014047 A1 | 1/2003 | Woloszko et al. | 606/41 |
| 2003/0028189 A1 | 2/2003 | Woloszko et al. | 604/45 |
| 2003/0088245 A1 | 5/2003 | Woloszko et al. | 606/41 |
| 2003/0130655 A1 | 7/2003 | Woloszko et al. | 606/45 |
| 2003/0130738 A1 | 7/2003 | Hovda et al. | 623/17.11 |
| 2003/0158545 A1 | 8/2003 | Hovda et al. | 606/32 |
| 2003/0171743 A1 | 9/2003 | Tasto et al. | 606/32 |
| 2003/0208194 A1 | 11/2003 | Hovda et al. | 606/41 |
| 2003/0208196 A1 | 11/2003 | Stone | 606/41 |
| 2003/0212395 A1 | 11/2003 | Woloszko et al. | 606/32 |
| 2003/0212396 A1 | 11/2003 | Eggers et al. | 606/41 |
| 2003/0216726 A1 | 11/2003 | Eggers et al. | 604/41 |
| 2004/0024399 A1 | 2/2004 | Sharps et al. | 606/32 |
| 2004/0049180 A1 | 3/2004 | Sharps et al. | 606/32 |
| 2004/0054366 A1 | 3/2004 | Davison et al. | 606/45 |
| 2004/0087937 A1 | 5/2004 | Eggers et al. | 606/41 |
| 2004/0116922 A1 | 6/2004 | Hovda et al. | 606/41 |
| 2004/0127893 A1 | 7/2004 | Hovda | 606/41 |
| 2004/0153057 A1 | 8/2004 | Davison | 600/410 |
| 2004/0186469 A1 | 9/2004 | Woloszko et al. | 606/41 |
| 2004/0230190 A1 | 11/2004 | Dahla et al. | 604/41 |
| 2005/0004634 A1 | 1/2005 | Ricart et al. | 606/41 |
| 2005/0010205 A1 | 1/2005 | Hovda et al. | 606/32 |
| 2005/0055019 A1* | 3/2005 | Skarda | 606/41 |
| 2005/0107782 A1* | 5/2005 | Reschke | 606/42 |
| 2005/0119650 A1 | 6/2005 | Sanders et al. | 424/426 |
| 2005/0131402 A1 | 6/2005 | Ciarrocca et al. | 600/450 |
| 2005/0187543 A1 | 8/2005 | Underwood et al. | 606/41 |
| 2005/0234439 A1 | 10/2005 | Underwood et al. | 606/32 |
| 2005/0251134 A1 | 11/2005 | Woloszko et al. | 606/32 |
| 2005/0261754 A1 | 11/2005 | Woloszko et al. | 606/32 |
| 2005/0288665 A1 | 12/2005 | Woloszko et al. | 606/41 |
| 2006/0036237 A1 | 2/2006 | Davison et al. | 606/41 |
| 2006/0095026 A1 | 5/2006 | Hovda et al. | 606/32 |
| 2006/0095145 A1 | 5/2006 | Ormsby | 606/34 |
| 2006/0129145 A1 | 6/2006 | Ormsby et al. | 606/41 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0001088 A1 | 1/2007 | Bowman | 606/41 |
| 2007/0010808 A1 | 1/2007 | Dahla | 606/41 |
| 2007/0010809 A1 | 1/2007 | Hovda et al. | 606/41 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2007/0208334 A1 | 9/2007 | Woloszko et al. | 606/41 |
| 2007/0208335 A1 | 9/2007 | Woloszko et al. | 606/41 |
| 2007/0213700 A1 | 9/2007 | Davison et al. | 606/32 |
| 2007/0282323 A1 | 12/2007 | Woloszko et al. | 606/41 |
| 2008/0243117 A1 | 10/2008 | Sharps et al. | 606/41 |
| 2010/0114110 A1 | 5/2010 | Taft et al. | 600/184 |
| 2010/0204693 A1 | 8/2010 | Sanders et al. | 606/41 |

FOREIGN PATENT DOCUMENTS

| | | |
|---|---|---|
| EP | 515 867 | 12/1992 |
| EP | 0703461 A2 | 3/1996 |
| EP | 0740926 A2 | 11/1996 |
| EP | 0 754 437 | 1/1997 |
| EP | 719162 B1 | 11/1997 |
| EP | 774926 B1 | 6/1999 |
| EP | 0 694 290 | 11/2000 |
| FR | 2313949 | 1/1977 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| JP | 57-57802 | 4/1982 |
| JP | 57-117843 | 7/1982 |
| JP | 2002-503508 | 2/2002 |
| JP | 2002-541904 | 12/2002 |
| NL | 05/000434 | 12/2006 |
| WO | 90/03152 | 4/1990 |
| WO | 90/07303 | 7/1990 |
| WO | 92/21278 | 12/1992 |
| WO | 93/13816 | 7/1993 |
| WO | 93/20747 | 10/1993 |
| WO | 94/04220 | 3/1994 |
| WO | 94/08524 | 4/1994 |
| WO | 94/08654 | 4/1994 |
| WO | 94/14383 | 7/1994 |
| WO | 94/26228 | 11/1994 |

| | | |
|---|---|---|
| WO | 95/05781 | 3/1995 |
| WO | 95/05867 | 3/1995 |
| WO | 95/34259 | 12/1995 |
| WO | 96/00042 | 1/1996 |
| WO | 96/07360 | 3/1996 |
| WO | 96/20652 | 7/1996 |
| WO | 96/23449 | 8/1996 |
| WO | 96/39914 | 12/1996 |
| WO | 96/41574 | 12/1996 |
| WO | 97/00070 | 1/1997 |
| WO | 97/00646 | 1/1997 |
| WO | 97/00647 | 1/1997 |
| WO | 97/23169 | 7/1997 |
| WO | 97/24073 | 7/1997 |
| WO | 97/24074 | 7/1997 |
| WO | 97/24992 | 7/1997 |
| WO | 97/24993 | 7/1997 |
| WO | 97/24994 | 7/1997 |
| WO | 97/48345 | 12/1997 |
| WO | 97/48346 | 12/1997 |
| WO | 98/00070 | 1/1998 |
| WO | 98/01087 | 1/1998 |
| WO | 98/03117 | 1/1998 |
| WO | 98/03220 | 1/1998 |
| WO | 98/07468 | 2/1998 |
| WO | 98/11944 | 3/1998 |
| WO | 98/14131 | 4/1998 |
| WO | 98/17190 | 4/1998 |
| WO | 98/27879 | 7/1998 |
| WO | 98/27880 | 7/1998 |
| WO | 99/03414 | 1/1999 |
| WO | 99/20185 | 4/1999 |
| WO | 99/42037 | 8/1999 |
| WO | 99/47058 | 9/1999 |
| WO | 99/51155 | 10/1999 |
| WO | 99/51158 | 10/1999 |
| WO | 00/07507 | 2/2000 |
| WO | 00/10475 | 3/2000 |
| WO | 00/62698 | 10/2000 |
| WO | 00/71043 | 11/2000 |
| WO | 01/26570 | 4/2001 |
| WO | 01/87154 | 5/2001 |
| WO | 01/82813 | 11/2001 |
| WO | 02/11635 | 2/2002 |
| WO | 02/36028 | 5/2002 |
| WO | 03/024506 | 3/2003 |
| WO | 2004/022155 | 3/2004 |
| WO | 2005/039390 | 5/2005 |
| WO | 2005/122938 | 12/2005 |
| WO | 2005/125287 | 12/2005 |

OTHER PUBLICATIONS

Codman & Shurtleff, Inc. "The Malis Bipolar Coagulating and Bipolar Cutting System CMC-II" brochure, early, 2pgs, 1991.
Codman & Shurtleff, Inc. "The Malis Bipolar Electrosurgical System CMC-III Instruction Manual", 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" Bio-Medical Engineering vol. 4, pp. 206-216, May 1969.
Elsasser, V.E. et al., "An Instrument for Transurethral Resection without Leakage of Current" Acta Medicotechnica vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" IEEE pp. 58-65, 1975.
Kramolowsky et al. "The Urological App of Electorsurgery" J. of Urology vol. 146, pp. 669-674, 1991.
Kramolowsky et al. "Use of 5F Bipolar Electrosurgical Probe in Endoscopic Urological Procedures" J. of Urology vol. 143, pp. 275-277, 1990.

Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," Am J. Cardiol vol. 60, pp. 1117-1122, Nov. 1, 1987.
Malis, L., "Electrosurgery, Technical Note," J. Neursurg., vol. 85, 970-975, Nov. 1996.
Malis, L., "Excerpted from a seminar by Leonard I. Malis, M.D. at the 1995 American Association of Neurological Surgeons Meeting," 1pg.
Malis, L., "Instrumentation for Microvascular Neurosurgery" Cerebrovascular Surgery, vol. 1, 245-260, 1985.
Malis, L., "New Trends in Microsurgery and Applied Technology," Advanced Technology in Neurosurgery, 1-16, 1988.
Malis, L., "The Value of Irrigation During Bipolar Coagulation" See ARTC 21602, 1 pg, Apr. 9, 1993.
Nardella, P.C., SPIE 1068:42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" Gastroenterology vol. 74(3), pp. 527-534, 1978.
Protell et al., "Computer-Assisted Electrocoagulation: Bipolar v. Monopolar in the Treatment of Experimental Canine Gastric Ulcer Bleeding," Gastroenterology vol. 80, No. 3, pp. 451-455, 1981.
Ramsey et al., "A Comparison of Bipolar and Monopolar Diathermy Probes in Experimental Animals", Urological Research vol. 13, pp. 99-102, 1985.
Selikowitz et al., "Electric Current and Voltage Recordings on the Myocardium During Electrosurgical Procedures in Canines," Surgery, Gynecology & Obstetrics, vol. 164, 219-224, Mar. 1987.
Shuman, "Bipolar Versus Monopolar Electrosurgery: Clinical Applications," Dentistry Today, vol. 20, No. 12, 7 pgs, Dec. 2001.
Slager et al. "Spark Erosion of Arteriosclerotic Plaques" Z. Kardiol. 76:Suppl. 6, 67-71, 1987.
Slager et al. "Vaporization of Atherosclerotice Plaques by Spark Erosion" JACC 5(6):1382-6, Jun. 1985.
Swain, C.P., et al., "Which Electrode, A Comparison of four endoscopic methods of electrocoagulation in experimental bleeding ulcers" Gut vol. 25, pp. 1424-1431, 1987.
Tucker, R. et al. "A Comparison of Urologic Application of Bipolar Versus Monopolar Five French Electrosurgical Probes" J. of Urology vol. 141, pp. 662-665, 1989.
Tucker, R. et al. "In vivo effect of 5 French Bipolar and Monopolar Electrosurgical Probes on the Porcine Bladder" Urological Research vol. 18, pp. 291-294, 1990.
Tucker, R. et al., "Demodulated Low Frequency Currents from Electrosurgical Procedures," Surgery, Gynecology and Obstetrics, 159:39-43, 1984.
Tucker, R. et al., Abstract P14-11, p. 248, "A Bipolar Electrosurgical Turp Loop", Nov. 1989.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202.

Buchelt, et al. "Excimer Laser Ablation of Fibrocartilage: An In Vitro and In Vivo Study", Lasers in Surgery and Medicine, vol. 11, pp. 271-279, 1991.

Costello et al., "Nd: YAG Laser Ablation of the Prostate as a Treatment for Benign Prostatic Hypertrophy", Lasers in Surgery and Medicine, vol. 12, pp. 121-124, 1992.

Rand et al., "Effect of Elecctrocautery on Fresh Human Articular Cartilage", J. Arthro. Surg., vol. 1, pp. 242-246, 1985.

Saal et al., "Thermal Characteristics and the Lumbar Disc: Evaluation of a Novel Approach to Targeted Intradiscal Thermal Therapy", NASS-APS First Joint Meeting, Charleston SC, Apr. 1998.

PCT International Search Report for PCT/US99/03339, 1 pg, Mailed May 14, 1999.

PCT International Search Report for PCT/US99/17821, 1 pg, Mailed Oct. 19, 1999.

PCT International Search Report for PCT/US00/13706. 1 pg, Mailed Jul. 31, 2000.

PCT International Search Report for PCT/US00/28267, 1 pg, Mailed Mar. 23, 2001.

PCT International Search Report for PCT/US01/15728, 1 pg, Mailed Oct. 18, 2001.

PCT International Preliminary Examination Report for PCT/US01/15728, 4 pgs, Mailed Jan. 23, 2003.

PCT International Search Report for PCT/US02/29469, 1 pg, Mailed May 22, 2003.

PCT International Search Report for PCT/US03/27745, 1 pg, Mailed Jul. 2, 2004.

PCT International Search Report for PCT/US05/20774 1 pg, Mailed Oct. 26, 2005.

PCT Written Opinon of the International Searching Authority for PCT/US05/20774, 4pgs, Mailed Oct. 26, 2005.

PCT International Search Report for PCT/US04/34949, 1 pg, Mailed Mar. 28, 2006.

PCT Written Opinon of the International Searching Authority for PCT/US04/34949, 3pgs, Mailed Mar. 28, 2006.

Supplementary EP Search Report for EP97932609, 2 pgs, Mailed Dec. 19, 2000.

EPO Communication, Supplementary EP Search Report for EP99934236, 3 pgs, Mailed Oct. 9, 2001.

EPO Communication, Supplementary EP Search Report for EP01935554, 5 pgs, Mailed Feb. 27, 2006.

EPO Communication, Supplementary EP Search Report for EP03749423, 3 pgs, Mailed Mar. 21, 2006.

EPO Communication, Supplementary EP Search Report for EP00936062, 6 pgs, Mailed Mar. 11, 2008.

PCT International Search Report and Written Opinion for PCT/US07/63198 10 pgs, Mailed Mar. 26, 2008.

BiLAP IFU 910033-002 Rev A for BiLAP Model 3527, L-Hook; BiLAP Model 3525, J-Hook; BiLAP Model 3529, High Angle, 2 pgs, Nov. 30, 1993.

BiLAP IFU 910026-001 Rev A for BiLAP Model 3525, J-Hook, 4 pgs, May 20, 1991.

BiLAP Generator Settings, Jun. 1991.

Tucker et al. "The interaction between electrosurgical generators, endroscopic electrodes, and tissue," Gastrointestinal Endoscopy, vol. 38, No. 2, pp. 118-122, 1992.

AESCULAP, "Flexible endoscope", Micro, Neuro and Spine surgery, 3 pgs.

Stoffels, E. et al., "Investigation on the Interaction Plasma-Bone Tissue", E-MRS Spring Meeting, 1 pg, Jun. 18-21, 2002.

Stoffels, E. et al., "Biomedical Applications of Plasmas", Tutorial presented prior to the 55th Gaseous Electronics Conference in Minneapolis, MN, 41 pgs, Oct. 14, 2002.

Stoffels, E. et al., "Plasma Interactions with Living Cells", Eindhoven University of Technology, 1 pg, 2002.

Stoffels, E. et al., "Superficial Treatment of Mammalian Cells using Plasma Needle", J. Phys. D: Appl. Phys. 26, pp. 2908-2913, Nov. 19, 2003.

Stoffels, E. et al., "Plasma Needle", Eindhoven University of Technology, 1 pg, Nov. 28, 2003.

Stoffels, E. et al., "Plasma Physicists Move into Medicine", Physicsweb, 1 pg, Nov. 2003.

Stoffels, E. et al., "Plasma Treated Tissue Engineered Skin to Study Skin Damage", Biomechanics and Tissue Engineering, Materials Technology, 1 pg, 2003.

Stoffels, E. et al., "Plasma Treatment of Dental Cavities: A Feasibility Study", IEEE Transaction on Plasma Science, vol. 32, No. 4, pp. 1540-1542, Aug. 2004.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.

Stoffels, E. et al., "Electrical and Optical Characterization of the Plasma Needle", New Journal of Physics 6, pp. 1-14, Oct. 28, 2004.

Stoffels, E. et al., "Where Plasma Meets Plasma", Eindhoven University of Technology, 23 pgs, 2004.

Stoffels, E. et al., "Gas Plasma effects on Living Cells", Physica Scripta, T107, pp. 79-82, 2004.

Stoffels, E. et al., "Plasma Treatment of Mammalian Vascular Cells: A Quantitative Description", IEEE Transaction on Plasma Science, vol. 33, No. 2, pp. 771-775, Apr. 2005.

Stoffels, E. et al., "Deactivation of *Escherichia coli* by the Plasma Needle", J. Phys. D: Appl. Phys. 38, pp. 1716-1721, May 20, 2005.

Stoffels, E. et al., "Development of a Gas Plasma Catheter for Gas Plasma Surgery", XXVIIth ICPIG, Endoven University of Technology, pp. 18-22, Jul. 2005.

Stoffels, E. et al., "Development of a Smart Positioning Sensor for the Plasma Needle", Plasma Sources Sci. Technol. 15, pp. 582-589, Jun. 27, 2006.

Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of Excherichia coli and *Streptococcus mutans*", IEEE Transaction on Plasma Science, vol. 34, No. 4, pp. 1325-1330, Aug. 2006.

Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for In Vivo Medical Treatment: Recent Developments and Perspectives", Plasma Sources Sci. Technol. 15, pp. S169-S180, Oct. 6, 2006.

* cited by examiner

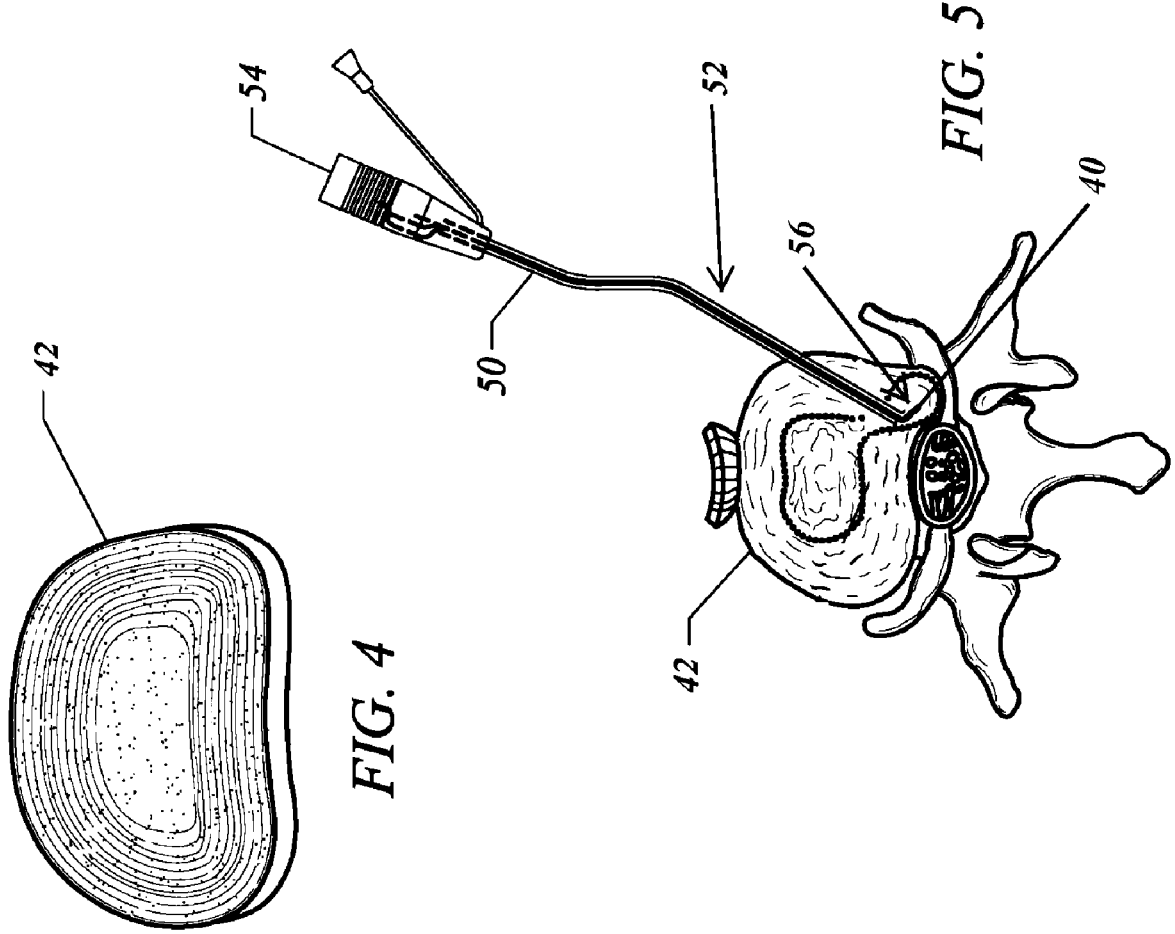
FIG. 5
FIG. 4
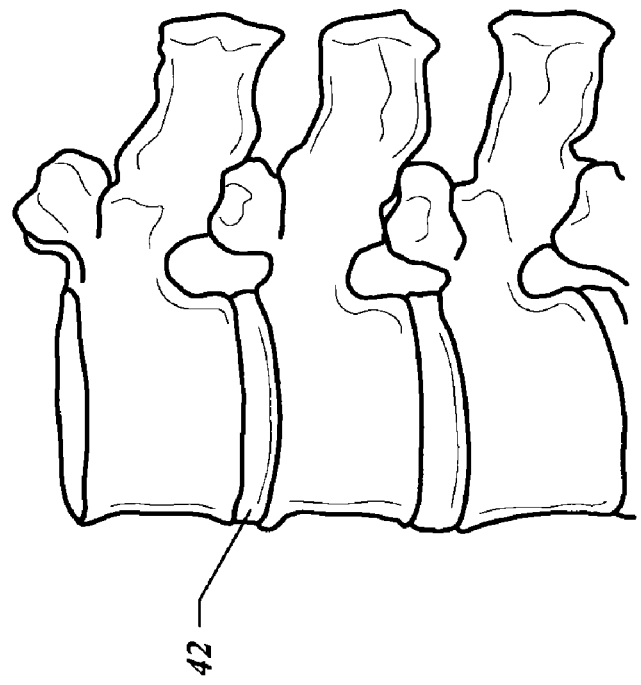
FIG. 3

US 7,901,403 B2

INTERNALLY LOCATED RETURN ELECTRODE ELECTROSURGICAL APPARATUS, SYSTEM AND METHOD

RELATED APPLICATION

This application is a continuation-in-part of U.S. patent application Ser. No. 11/367,254 filed Mar. 2, 2006, the complete disclosure of which is incorporated herein by reference for all purposes.

FIELD OF INVENTION

This invention pertains to an electrosurgical apparatus, system and method of treating tissue in a body structure, in particular a bipolar, plasma-generating electrosurgical apparatus and system wherein the return electrode is enclosed within an electrosurgical shaft, and the active electrode is located on the outside surface of the shaft such that in treating the tissue, the tissue is exposed to plasma generated on the active electrode, but minimally exposed to localized electric fields generated between the active and return electrodes. In various embodiments, due to the configuration of the electrodes, the electric fields are directed away from the target tissue, as they are oriented inwardly towards the return electrode within the shaft, thereby avoiding electrical stimulation of neuromuscular structures in the tissue by these electric fields.

BACKGROUND

Electrosurgical instruments and systems comprising an active and return electrode and powered by a radio-frequency voltage supply as is illustrated for example in FIG. 1, are widely used in procedures for treating target tissues in the body. Treatment of the target tissue involves placing the electrodes (10) in close proximity to a target tissue (12) and applying power to the electrodes to cause Coblation™, heating, ablation, coagulation, cutting, removal, puncturing, probing, and otherwise stimulating the tissue. In some systems an electrically conductive fluid is supplied between the electrodes to generate plasma to treat the tissue; in other systems, the body's fluids are used as the conductive fluid. An example of such system for treating tissues with plasma is described in commonly assigned U.S. patent application Ser. No. 10/661,118, hereby incorporated herein by reference for all purposes.

In an electrosurgical system as illustrated in FIG. 1, the electrodes are located on the distal end portion of the shaft (14). In one configuration of the distal end portion of the shaft as is illustrated in detail FIG. 2, the return electrode (16) is positioned on the outside perimeter of the shaft and, in various embodiments, surrounds the active electrode (18) which is within the shaft. To ensure that plasma (20) generated on the active electrode is closest to the tissue, the distal tip of the active electrode projects beyond the return electrode. Also, in the embodiment illustrated in FIG. 2, the active electrode is separated from the return electrode by an insulator (24), and electrically conductive fluid (26) is supplied between the electrodes by a fluid lumen (27) circumferentially positioned on the shaft around the return electrode. This conductive fluid as is illustrated in FIG. 2 forms a conductive fluid pathway (38) between the electrodes.

Also in an electrosurgical system as is illustrated in FIG. 2 and as will be appreciated by one ordinarily skilled in the art, when power is applied across the electrodes, an electric field (22) sometimes in the order of 30,000 V/cm is generated which, for some procedures, is not desired as these fields can interact with the tissue and cause electrical stimulation of neuromuscular structures (28) within the tissue.

Accordingly, there is a need for apparatus and systems for use in electrosurgical procedures wherein unwanted electrical stimulation of the tissue is avoided, and which can be used in confined spaces within the body.

SUMMARY OF THE INVENTION

The present electrosurgical system in one embodiment is a system for performing an electrosurgical procedure on a body tissue using plasma such that electrical stimulation of the tissue is minimized, the system comprising: an electrosurgical instrument comprising a shaft; an electrically conductive fluid supply having a discharge port on a distal end portion of the shaft; and a radio-frequency voltage supply connected to the electrosurgical instrument. In one embodiment, the shaft has: an active electrode on the distal end portion; a return electrode recessed within the shaft; an electrical insulator separating the active and return electrode. Within the shaft is a chamber in communication with the active and return electrodes such that on applying the radio-frequency voltage supply to the active and return electrodes in the presence of an electrically conductive fluid, plasma is generated on the active electrode on the surface of the shaft, and electric fields generated between the active and return electrodes are directed within the shaft, and thus away from the tissue.

The present electrosurgical system in one embodiment is a system for performing an electrosurgical procedure on a body tissue using plasma such that electrical stimulation of the tissue is minimized, the system comprising: an electrosurgical instrument comprising a shaft; an electrically conductive fluid supply having a discharge port on a distal end of the shaft; and a radio-frequency voltage supply connected to the electrosurgical instrument. In one embodiment, the shaft comprises: an active electrode on the distal end; a return electrode recessed within the shaft; an electrical insulator separating the active and return electrode. Within the shaft is a chamber in communication with the active and return electrodes such that on applying the radio-frequency voltage supply to the active and return electrodes in the presence of an electrically conductive fluid, plasma is generated on the active electrode on the surface of the shaft, and electric fields generated between the active and return electrodes are directed within the shaft, and thus away from the tissue. In some embodiments the shaft of the electrosurgical instrument may include an aspiration lumen having a plurality of inlet apertures formed along a selected length of the shaft, where the selected length of the shaft include a first portion for insertion within a target tissue structure, such as an intervertebral disc, and a second portion for venting outside the target tissue structure.

The present electrosurgical method in one embodiment is a method of treating tissue that avoids nerve stimulation, comprising the steps of: positioning a distal end portion of an electrosurgical instrument in close proximity to the tissue, the distal end portion comprising an active electrode and a return electrode; applying a radio frequency voltage across the active and return electrodes in the presence of an electrically conducting fluid sufficient to generate plasma on the active electrode; and contacting the tissue with the plasma such that the tissue is exposed to plasma but minimally exposed to electric fields generated between the active electrode and the return electrode.

In various embodiments the present apparatus and system can be used in procedures for treating highly neutralized tissue, and other tissues located in confined targets within the body. An example of such targets is tissue in the intervertebral discs.

Details of embodiments of the present apparatus, system and methods are illustrated and described the following Figures and specifications.

BRIEF DESCRIPTION OF THE DRAWINGS

FIG. 3 is an illustration of lateral view of a partial spinal column.

FIG. 4 is an illustration of a perspective view of an intervertebral disc.

FIG. 5 is an illustration of an embodiment of the present apparatus within a herniated intervertebral disc for treating the disc in accordance with one orientation of the apparatus.

DETAILED DESCRIPTION

Figure 1:
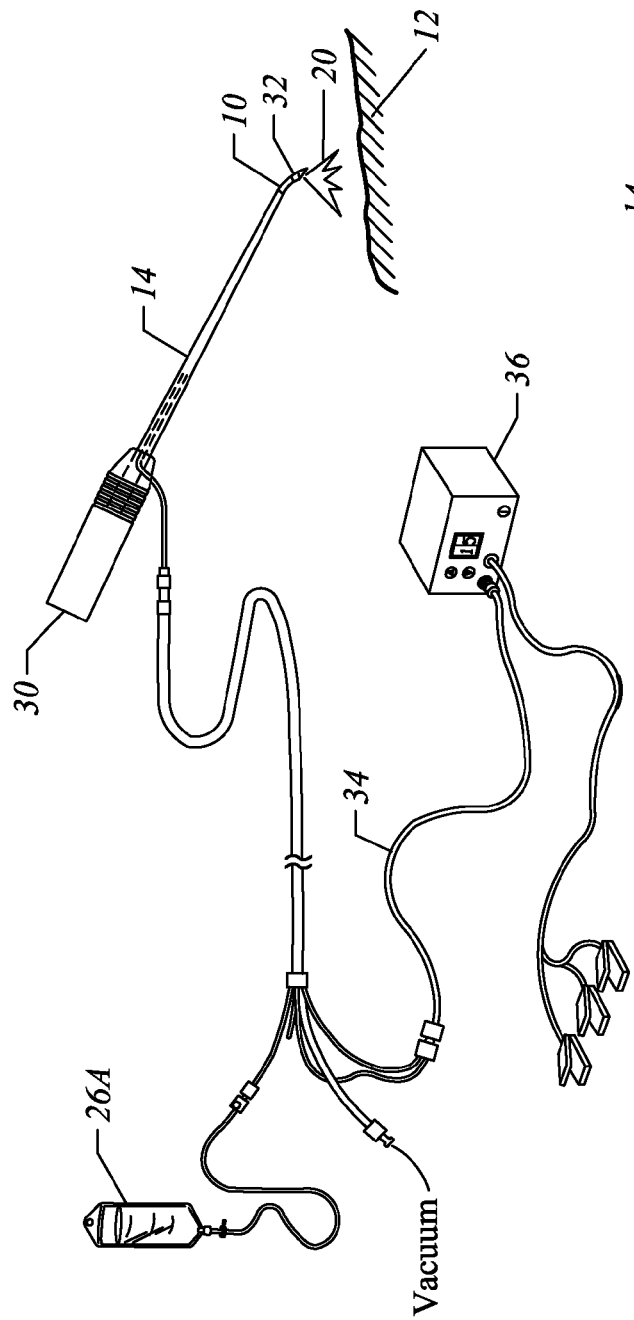
FIG. 1 is an illustration of a bipolar electrosurgical system.
Figure 2:
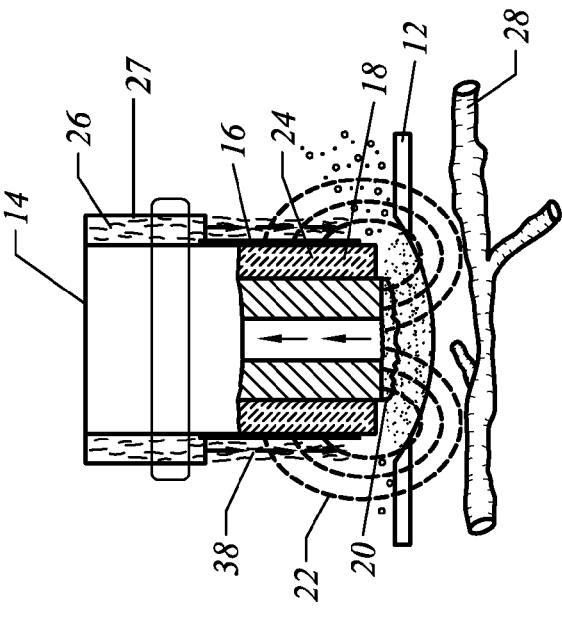
FIG. 2 is an illustration of a cross-section of the distal end portion of an electrosurgical instrument showing plasma and electrical fields between the active and return electrodes.
Figure 7:
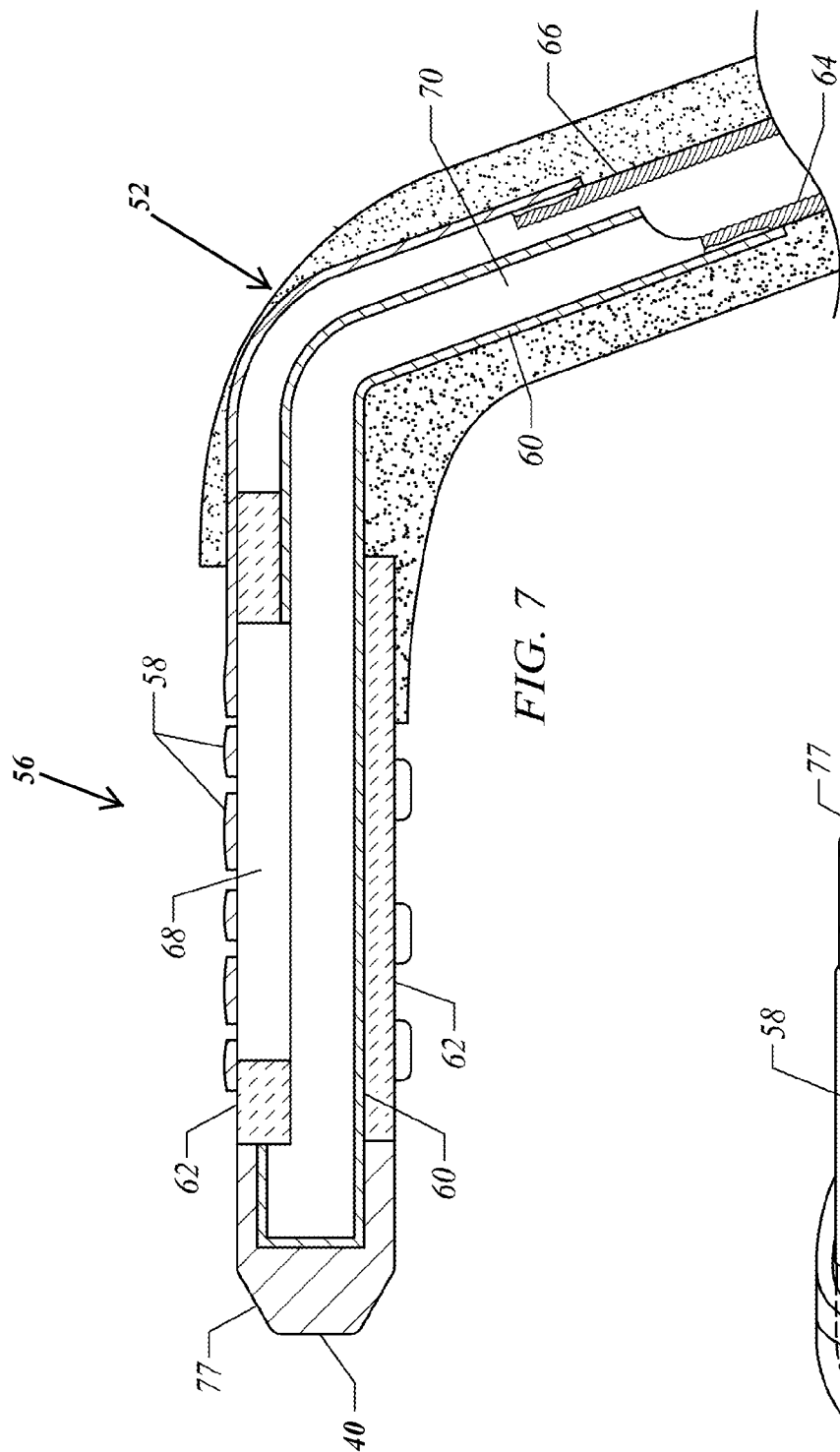
FIG. 7 is an illustration of a longitudinal cross-sectional view of the distal end portion of the present electrosurgical shaft.
Figure 6:
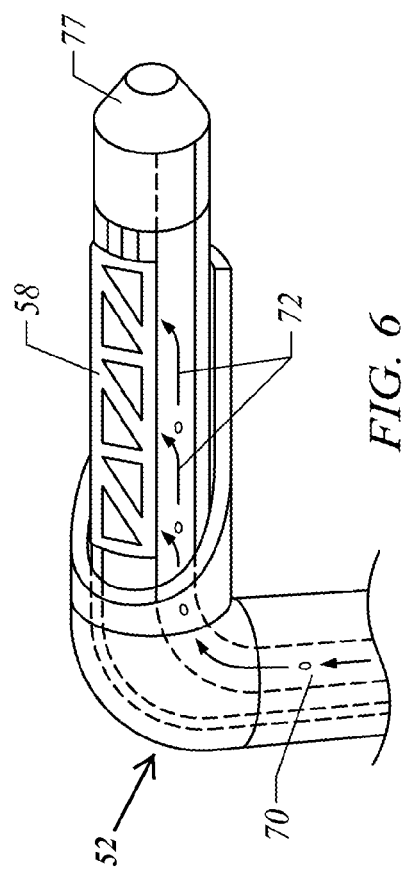
FIG. 6 is an illustration of a perspective cut-away view of the distal end portion of the present electrosurgical shaft.
Figure 8:
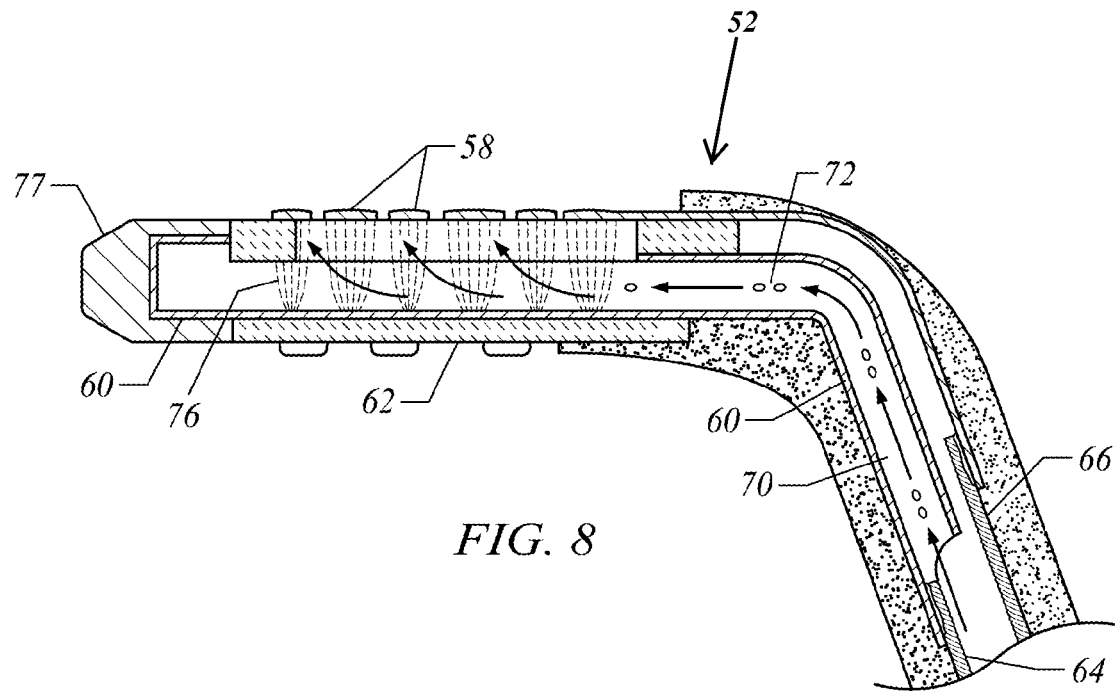
FIG. 8 is an illustration of the cross-section of the distal end portion of the present apparatus showing conductive fluid and electrical fields between the active and return electrodes, without plasma.

With reference to FIGS. 1 and 2, a plasma-generating bipolar electrosurgical system typically comprises an electrosurgical shaft (14) having proximal (30) and distal (32) end portions; one or more active electrode(s) (18) located on the distal end of the shaft; a return electrode (16) located on the shaft of the return electrode and separated from the active electrode by an insulator (24); electrical connectors (34) coupling the active and return electrodes (18, 16) to a source of radio-frequency voltage supply (36); and a supply of electrically conductive fluid (26) from fluid reservoir (26a) adapted to be discharged between the active and return electrodes. On application of the radio-frequency voltage across the electrodes in the presence of the conductive fluid, plasma is generated which can be used to treat tissue as described for example in U.S. patent application Ser. No. 10/661,118, supra.

A bipolar electrosurgical apparatus, as is illustrated for example in FIGS. 1 and 2, is an electrosurgical apparatus wherein both the active and return electrodes (18, 16) are positioned on the shaft (14). In this regard, a bipolar apparatus is distinguishable from a monopolar apparatus in that on a monopolar apparatus only the active electrode is positioned on the shaft; in a monopolar apparatus the return electrode is located off the shaft but is in electrical contact through the patient to the target site and the electrically conductive fluid.

Examples of an electrically conductive fluid include isotonic saline, a conductive gel, Ringer's solution and the biocompatible electrolytes as described for example in U.S. patent application Ser. No. 10/661,118, supra.

In a bipolar electrosurgical apparatus as is illustrated for example in one embodiment in FIG. 2, the electrodes are separated from each other by an insulator (24) to prevent short-circuiting of the electrodes on the distal end portion of the shaft. However, to establish a closed electrical circuit across the electrodes on the shaft and generate plasma, an electrically conductive fluid pathway (38) is provided between the electrodes. This electrically conductive fluid pathway can be provided in several ways including placing the conductive fluid on the shaft such that the fluid is in contact with both electrodes; or placing the conductive fluid on the target tissue such that the fluid is in contact with both electrodes and the target tissue at the same time; or inserting the shaft into the tissue such that the electrical circuit between the electrodes is established through the tissue by conductive body fluids in the tissue.

In both bipolar and monopolar plasma-generating apparatus, however, regardless of how the conductive pathway is established between the electrodes, for the instrument to generate plasma it is necessary to maintain a closed electrical circuit on the distal end of the shaft comprising the electrodes, the electrically conductive fluid and the power supply, as described for example in U.S. patent application Ser. No. 10/661,118, supra.

On a bipolar plasma-generating systems and apparatus as illustrated in FIGS. 1 and 2 and as is described in commonly assigned U.S. patent application Ser. No. 10/661,118, supra, plasma is generated on the electrodes by applying a radio frequency voltage across the electrodes in the presence of the electrically conductive fluid (26) alone fluid pathway (38). With these systems and apparatus, plasma (20), comprised of energized charged species such as ions and electrons, is used to treat the target tissue by Coblation® as described in U.S. patent application Ser. no. 10/661,118, supra.

On a plasma-generating bipolar apparatus, in order to generate and use plasma to treat the tissue, the electrodes are designed such that only the active electrode generates the plasma, and that in use this electrode is located as close as possible to the target tissue. Conversely, the return electrode is designed such that it does not generate plasma, and that in use it is away from the target tissue to avoid contacting the tissue, but it is in electrical contact with the active electrode through the electrically conductive fluid. One way by which the plasma is generated on the active electrodes but not on the return electrode is to maintain the surface area of the active electrode smaller relative to the surface area of the return electrode.

In this regard it should be noted that during use, ablated tissues and other materials may accumulate on the return electrode thereby causing a reduction of its exposed surface area relative to the exposed surface area of the active electrode, thereby undesirably causing the return electrode to also generate plasma.

In a plasma-generating bipolar apparatus and system as is illustrated for example in FIGS. 1 and 2 and described in U.S. patent application Ser. No. 10/661,118, supra, a convenient way by which a relatively large return electrode is maintained is to use the shaft proximal of the active electrode as the return electrode. Typically this involves using an outer metallic portion of the shaft that is insulated from the active electrode. Thus, as is illustrated in FIG. 2 in a bipolar system, in one embodiment, the active electrode is the distal tip of the shaft, whereas the return electrode is the shaft's outer surface insulated from the active electrode.

Also as is illustrated for example in FIGS. 1 and 2 and described in U.S. patent application Ser. No. 10/661,118, supra, in using a plasma-generating bipolar apparatus for some procedures it is necessary to supply the electrodes with an electrically conductive fluid to form the electrically conductive fluid (26) alone fluid pathway (38) between the electrodes (18, 16), and in some embodiments also to flush the target site and the electrodes with fluid.

In procedures requiring a conductive fluid, this fluid can be provided by a fluid supply lumen located on the shaft. In this arrangement the fluid supply lumen is attached to a conductive fluid supply at the proximal end, such that the fluid is available for discharge at the distal end through an opening in the lumen near the electrodes and the target site.

Further, in a plasma-generating bipolar apparatus as is illustrated for example in FIGS. 1 and 2, for some procedures it is necessary to remove excess fluids and ablated tissue away from the target site. Where such fluid and tissue removal is necessary, an aspiration lumen is provided. In various embodiments the fluid aspiration lumen is located on the shaft but it can also be placed off the shaft in other embodiments. In an arrangement wherein the aspiration lumen is on the shaft, the lumen may comprise of a fluid inlet port disposed at the distal end of shaft, and a fluid discharge port at the proximal end where it is connected to a vacuum system for suctioning fluids, gases and ablated tissue from the target site through the aspiration lumen.

One procedure wherein a bipolar, plasma-generating apparatus is used for treating tissue is in treating an intervertebral disc as is described for example in U.S. patent application Ser. No. 10/656,597, incorporated herein by reference herein for all purposes. In one procedure as illustrated in FIGS. 3-5, the distal end of the shaft (40) is inserted in the disc (42) and thereafter radio-frequency voltage is applied across the electrodes to generate plasma to treat the disc. In FIG. 5, the electrosurgical apparatus (50) is shown inserted anteriorily into the disc, however as will be appreciated to one ordinarily skilled in the art, in other procedures not shown in FIG. 5, the electrosurgical apparatus is also insertable posteriorily into the disc.

As can be appreciated in the art in using a bipolar apparatus in treating a intervertebral disc as is illustrated in FIGS. 3-5, besides generating plasma as described above, the apparatus also generates electrical fields (22) across the electrodes as is illustrated in FIG. 2, and these fields can be as high as 30,000 V/cm. A problem with these electrical fields is that in sensitive tissues such as in the disc and around the spine, the electric fields can cause undesired stimulation of regional nerve or nerve fibers (28) as is illustrated in FIG. 2.

Also as can be appreciated by one ordinarily skilled in the art, in treating tissue in confined spaces such as in the intervertebrate disc, it can be difficult to avoid contacting the tissue with the return electrode thus causing a short circuit across the electrodes or reducing the surface area of the electrode relative to the area of the active electrode.

Another problem with using a bipolar apparatus in confined spaces such as in the invertebrate disc is that since the shaft may include a fluid supply lumen and an aspiration lumen, the shaft can get too bulky for easy access and use.

Accordingly, the present apparatus, system and apparatus in various embodiments are adapted to electrosurgically treat tissue, while minimizing exposure of the tissue to electrical stimulation. The apparatus, as will be appreciated from the present description, is also reduced in size in part because of the placement of the return electrode with the shaft; thus, with a smaller profile on the distal end portion the present apparatus and system provides improved access flexibility for applying electrosurgical procedures in restricted areas of the body, as for example, within an intervertebral disc.

With reference to FIG. 5-11, in one embodiment the electrosurgical apparatus (50) comprises a shaft (52) having a proximal end portion (54) and a distal end portion (56). On the distal end portion of the shaft is disposed an active electrode (58) on the surface of the shaft. Also disposed on the distal end portion but within the shaft is a return electrode (60) that is insulated from the active electrode by an insulating member (62) positioned on the distal end portion of the shaft. In this position, the insulating member prevents direct electrical contact between the active and return electrodes. Also included in the shaft in the present embodiment are electrical conductors (64, 66) that are adapted for applying a radio-frequency voltage difference across the active and return electrodes.

Figure 11:
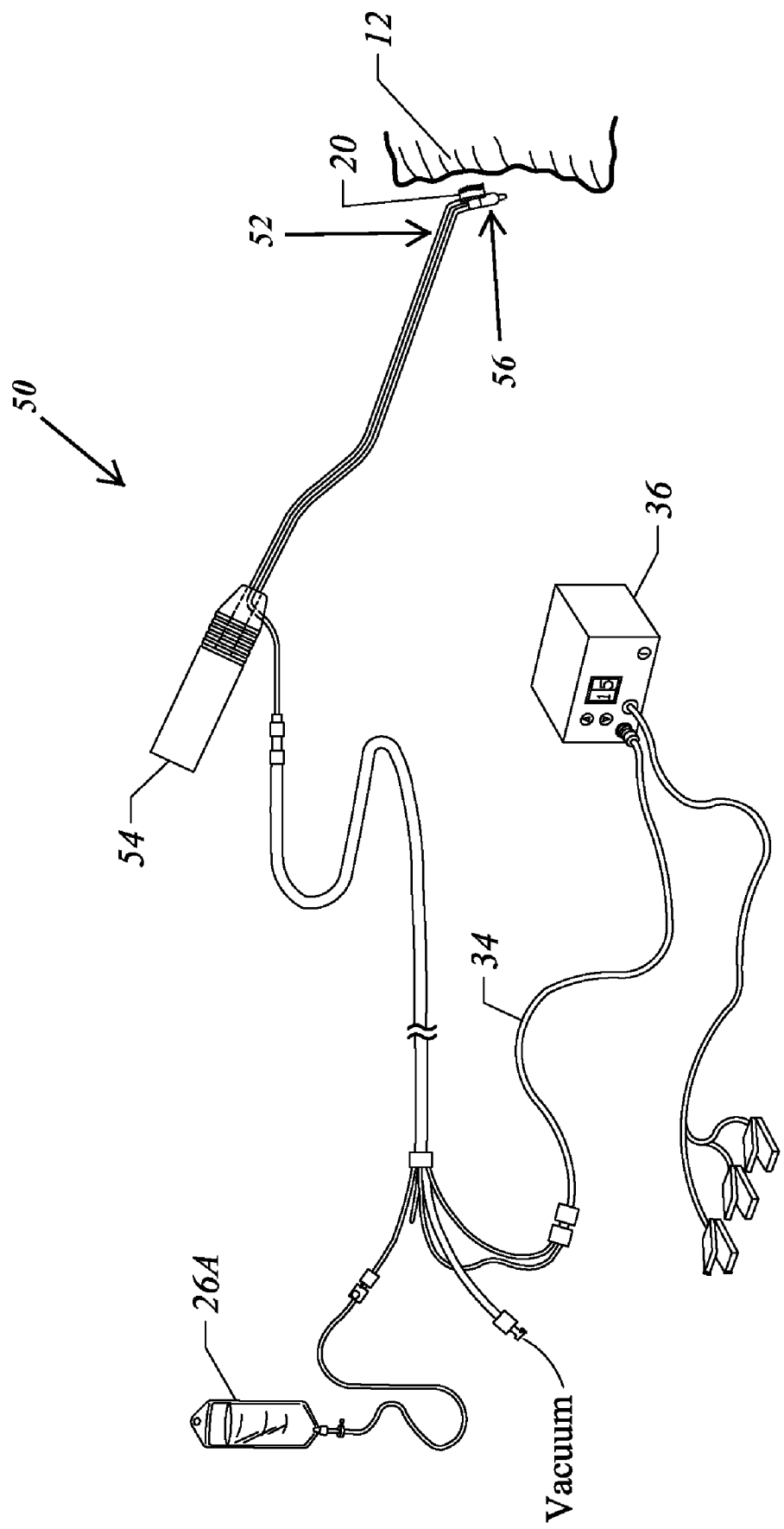
FIG. 11 is as illustration the present electrosurgical system wherein the return electrode is enclosed with the distal end portion of an electrosurgical shaft.

In one embodiment the electrosurgical apparatus comprises a lumen (70) within the shaft through which an electrically conductive fluid such as saline, Ringer's solution or another acceptable other biocompatible ionic solutions can be supplied to the distal end portion of the shaft in the vicinity of the electrodes and the target tissue. As is illustrated in FIGS. 1 and 11, the electrically conductive fluid can be supplied from a reservoir (26A) attached to the apparatus at the proximal end; in other embodiments not shown the reservoir is located on another apparatus.

Figure 9:
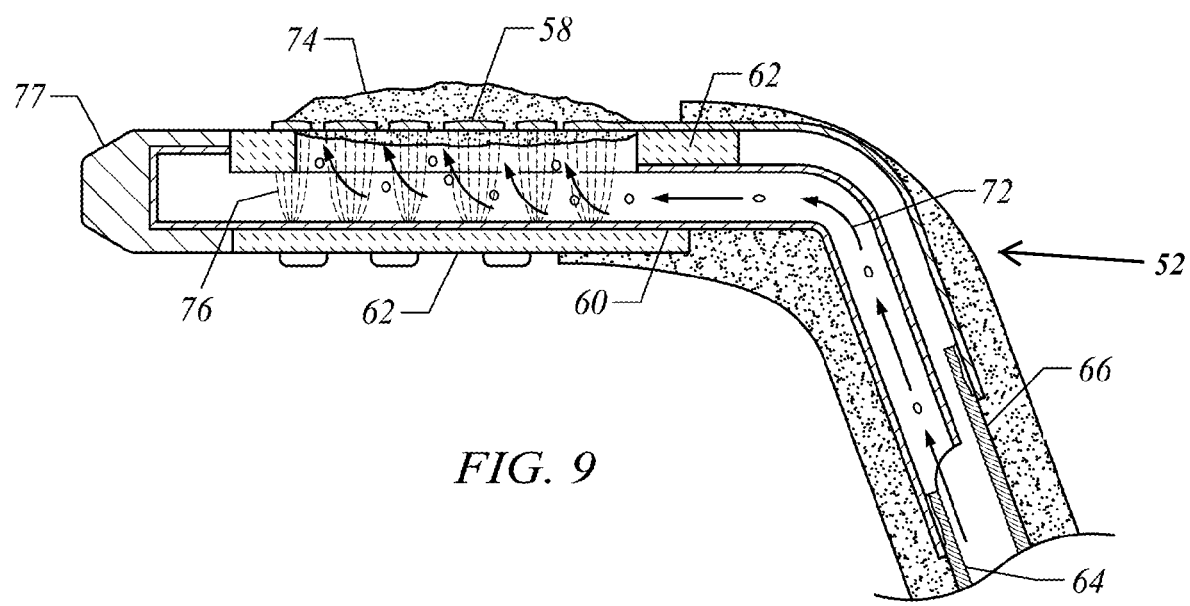
FIG. 9 is an illustration of the cross-section of the distal end portion of the present apparatus showing conductive fluid flow, electrical field lines between the active and return electrodes, with plasma on the active electrode.

In the embodiment illustrated in FIGS. 6-9, for example, the lumen is connected to an interconnecting passage (68) formed within the distal end portion of the shaft in between the electrodes. Within this interconnecting passage as is illustrated in FIG. 9, when a high frequency voltage is applied across the electrodes in the presence of an electrically conductive fluid, for example within the interconnecting passageway (68), plasma (74) which can be used to treat tissue is generated on the active electrode (58). Also, as noted above, when the power is applied to the electrodes, an electric field (76) is generated between the active electrode (58) and the return electrode (60) located within the shaft (52). Thus, since these electric fields are directed inwards, their effect on neighboring tissue is at least minimized, or eliminated.

Figure 10:
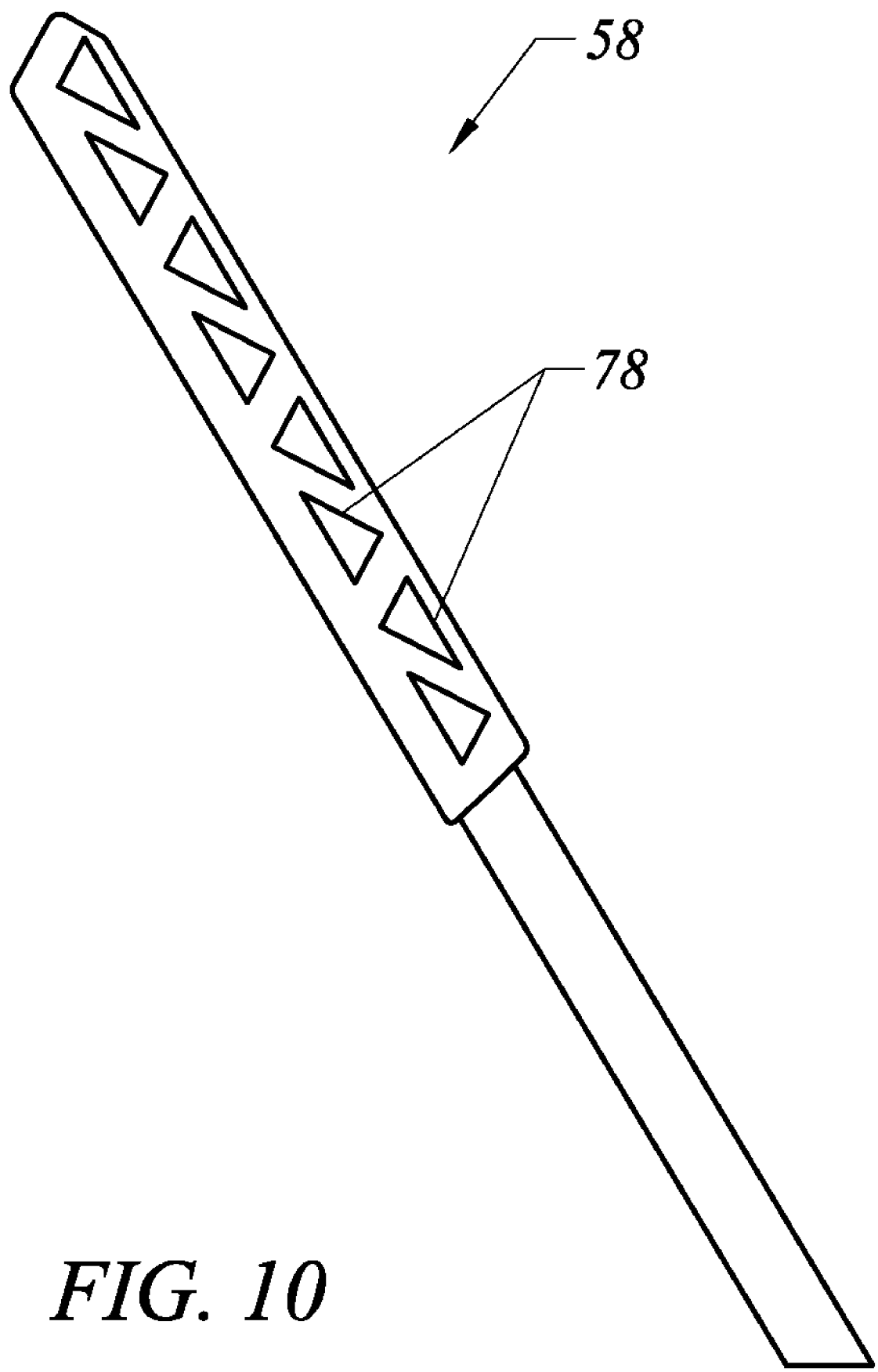
FIG. 10 is an illustration of a perspective view of an embodiment of the present active electrode.

In an embodiment of the active electrode illustrated in FIGS. 6-10, and in particular in FIG. 10, a plurality of apertures or holes (78) are provided on the electrode for passing an electrically conductive fluid between the outside of the shaft to the return electrode. In one embodiment the apertures are in the form of a mesh made of interwoven wires. Thus with this embodiment, both electrodes can be kept in electrical contact with an electrically conductive fluid within the interconnecting passageway (68).

Also in the embodiment of the apparatus illustrated in FIGS. 6-10, the return electrode is connected to a conductive cap (77) having an exposed surface on the outer surface of the shaft (52), such that the cap is spaced sufficiently far from the active electrode to minimize generation of an electric circuit between the active electrode and the cap. An advantage of using this cap is that if the cap is conductive, since it is connected to the return electrode, its conductive area contributes to the area of the return electrode and thus helps to ensure that the charge density on the surface of the return electrode is lower than the charge density on the surface of active electrode.

With reference to FIGS. 1 and 11, the electrosurgical apparatus in one embodiment comprises an aspiration lumen having an inlet in the proximity of the electrodes for removing fluids form the distal end portion of the shaft. The fluids may include fluids that flush the site as well as fluids that result from treatment of the tissue.

Also provided in the present application is a system for performing an electrosurgical procedure on a body tissue using plasma, as is illustrated for example in FIG. 11. The system (50) in one embodiment comprises an electrosurgical instrument comprising a shaft (52); an electrically conductive fluid supply having a discharge port on a distal end portion (56) of the shaft; and a radio-frequency voltage supply (36) connected to the electrosurgical instrument. In one embodiment, and as described above with reference to FIGS. 6-9, the shaft has: an active electrode (58) on the distal end portion; a return electrode (60) recessed within the shaft; an electrical insulator (62) separating the active and return electrode; and an interconnecting passageway (68) in communication with the active and return electrodes within the shaft, wherein on applying the radio-frequency voltage supply (36) to the active and return electrodes in the presence and electrically conductive fluid (72), plasma (74) is generated on the active electrode on the surface of the shaft, and electric fields (76) generated between the active and return electrodes are directed within the shaft.

Figure 12:
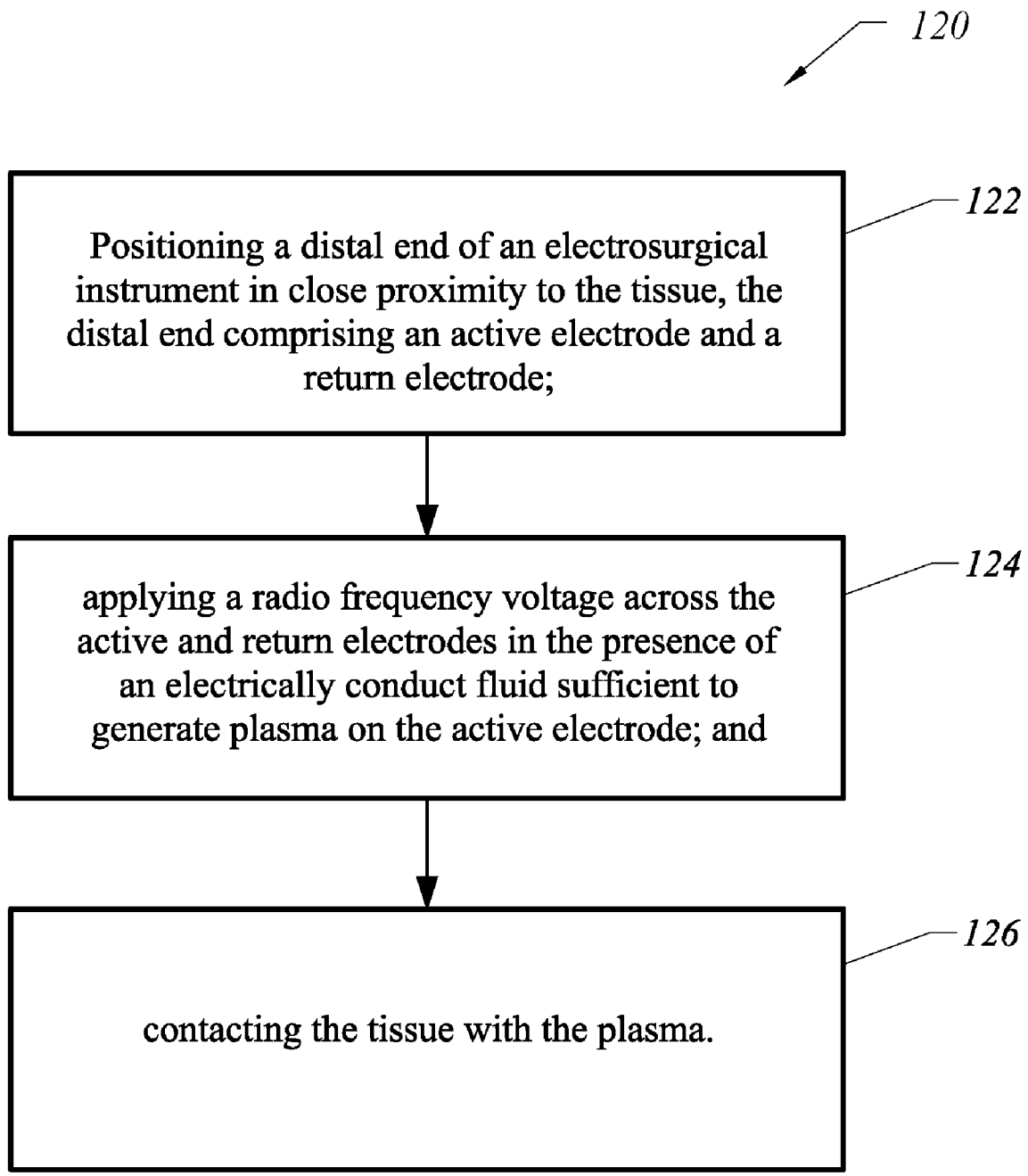
FIG. 12 is an algorithm of the present method of treating tissue with the present apparatus and system.

Further provided is a method of treating body tissue including nerve-sensitive tissue in the body, as set forth in FIG. 12, comprising the steps of: positioning a distal end portion of an electrosurgical instrument in close proximity to the tissue (122), the distal end portion comprising an active electrode and a return electrode; applying a radio frequency voltage across the active and return electrodes in the presence of an electrically conduct fluid sufficient to generate plasma on the active electrode; contacting the tissue with the plasma (124) and thereby avoiding exposing the tissue to electric fields generated between the active electrode and the return electrodes.

Now referring generally to the embodiments shown in FIGS. 13-16, an electrosurgical system (150) for insertion into a body structure (138) is provided. Electrosurgical system (150) generally includes shaft (152) having a distal end portion (156) and a proximal end (not expressly shown) where distal end portion (156) is adapted for treating a target tissue within body structure (138). In a preferred embodiment, body structure (138) may be an intervertebral disc and the target tissue comprises tissue within either or both the nucleus pulposus or the annulus fibrosus thereof. In the present embodiment distal end portion (156) includes an active electrode (158) disposed on the exterior surface of shaft (152). Also disposed within distal end portion (156) but within shaft (152) is a return electrode (160) that is insulated from the active electrode by an insulating member or spacer (162). In this position, insulating member (162) prevents direct electrical contact between active electrode (158) and return electrode (160) but also allows conductive fluid (172) to flow therebetween. Also included in shaft (152) are suitable electrical conductors (not expressly shown) adapted for connection with a radio-frequency voltage source and applying a radio-frequency voltage difference across active electrode (158) and return electrode (160) and a conductive cap (177), as described below.

In the present embodiment apparatus (150) comprises a fluid delivery lumen (170) and an aspiration lumen (171). Fluid delivery lumen (170) is preferably adapted to supply an electrically conductive fluid (172) such as saline, Ringer's solution or another suitable biocompatible ionic solutions to the distal end portion (156) of shaft (152) in the vicinity of the electrodes (158) and (160) and the target tissue. As is illustrated in FIGS. 1 and 11, electrically conductive fluid (172) may be supplied from a reservoir (26A) in communication with the apparatus (150) at the proximal end or from another suitable source of electrically conductive fluid. In the present embodiment the distal terminus of delivery lumen (170) comprises return electrode (160).

In the present embodiment fluid delivery lumen (170) is connected with and terminates within an interconnecting passage or chamber (168) formed within the distal end portion (156) of the shaft (152) between the active electrode (158) and return electrode (160). In other words, fluid delivery lumen (170) supplies fluid (172) to chamber (168) which may then preferably flow through apertures (178) of active electrode (158). Within chamber (168), when a suitable high frequency voltage is applied across the electrodes (158) and (160) in the presence of electrically conductive fluid (172) a plasma may preferably be formed for the treatment of tissue proximate active electrode (158).

Shaft (152) also includes aspiration lumen (171). In the present embodiment aspiration lumen (171) includes a distal opening (186) proximate active electrode (158), return electrode (160) and chamber (168) as well as a plurality of apertures (188) formed along a selected length (182) of shaft (152). In the present embodiment, apertures (188), which may also be referred to as "inlet apertures", are substantially uniformly spaced along selected length (182), including being uniformly spaced along the circumference of shaft (152), and have a uniform size. In alternate embodiments the size and disposition of apertures (188) may vary along the selected length. In the present embodiment, selected length (182) comprises approximately 2.5 centimeters, however in alternate embodiments selected length may be in the range of between about one centimeter and about five centimeters or between about two centimeters and about three centimeters.

Figure 14:
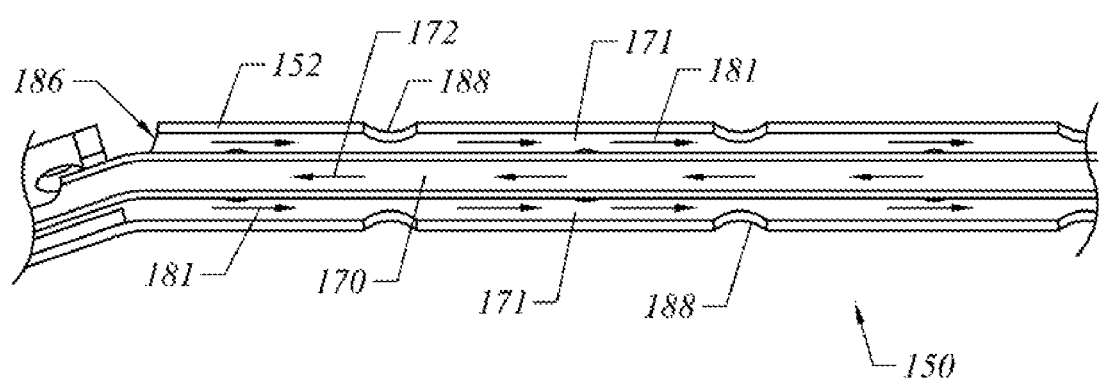
FIG. 14 shows a cut-away view of a portion of a shaft of an electrosurgical system.

As shown in the embodiment of FIG. 14, conductive fluid (172) is delivered through fluid delivery lumen (170) and fluids are vented from the treatment site via aspiration lumen (171). Fluids may enter aspiration lumen (171) through opening (186) or apertures (188) and subsequently travel away from the body structure (138) in the direction of arrows (181).

Figure 13:
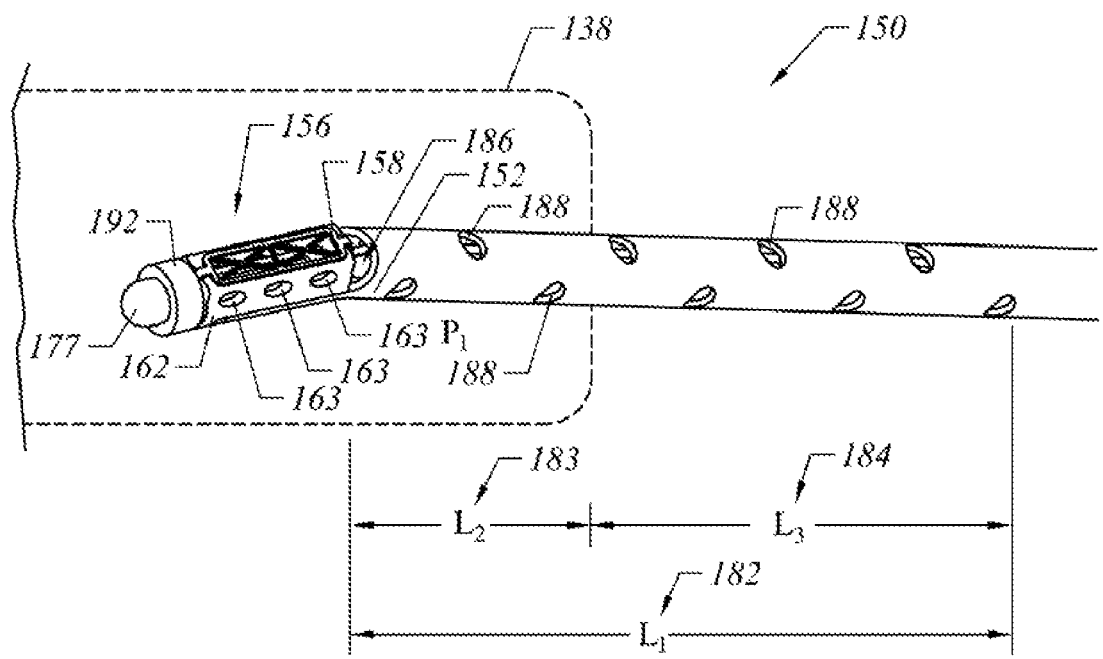
FIG. 13 shows an electrosurgical system for insertion according to the present disclosure for treating a target tissue.

Referring now to FIG. 13, the selected length (182) comprises a first portion (183) and a second portion (184) where the first portion (183) is designed to be inserted within body structure (138) during a medical procedure while the second portion (184) is designed to remain outside of the body structure during use. For example, first portion (183) may be about one (1) centimeter and second portion (184) may be about one and one-half (1.5) centimeters. In this manner, first portion (183) allows fluids (including gases) produced during treatment of the target tissue to evacuate through aspiration lumen (171) via apertures (188) and opening (186) along first portion (183). In an alternate embodiment (not expressly shown) the cumulative or collective area of apertures (188) with second portion (184) is at least equal to the cross sectional area of aspiration lumen (171). In another alternate embodiment, the size and/or distribution of apertures (188) in the first portion (183) may be greater than the size and/or distribution of apertures (188) in the second portion (184). In an alternate embodiment, distal opening 186 may be filled with an epoxy or other suitable material such that flow into aspiration lumen (180) is provided only through apertures (188).

By providing second portion (184) outside of body structure (138) pressure $P_1$ within body structure may be preferably kept at or substantially near atmospheric pressure. Aspiration lumen (180) may preferably be in communication with a suction source, however, the disposition of apertures (188) along selected length (182) allows fluid to flow away from the treatment site without requiring a separate suction source. In situations in which a separate suction source is not provided or not used, the evacuated material may exit aspiration lumen (171) via apertures along the second portion (184) of selected length (182).

As noted above, when the power is applied to electrodes (158) and (160), an electric field (not expressly shown) may be is generated therebetween. However, since this electric field is directed inwards and is maintained primarily within the distal end portion (156) the effect of the electric field on neighboring tissue is substantially minimized, if not eliminated.

In the embodiments of the apparatus illustrated in FIGS. 13-16, return electrode (160) is in electrical communication with a conductive cap or tip (177) having an exposed surface on the outer surface of the shaft (152), such that the cap is sufficiently spaced with respect to active electrode (158) to minimize generation of an electric field between the active electrode and the cap. As discussed above, an advantage of providing conductive cap (177) is to ensure that the charge density on the surface of return electrode (160) is lower than the charge density on the surface of active electrode (158).

Figure 15:
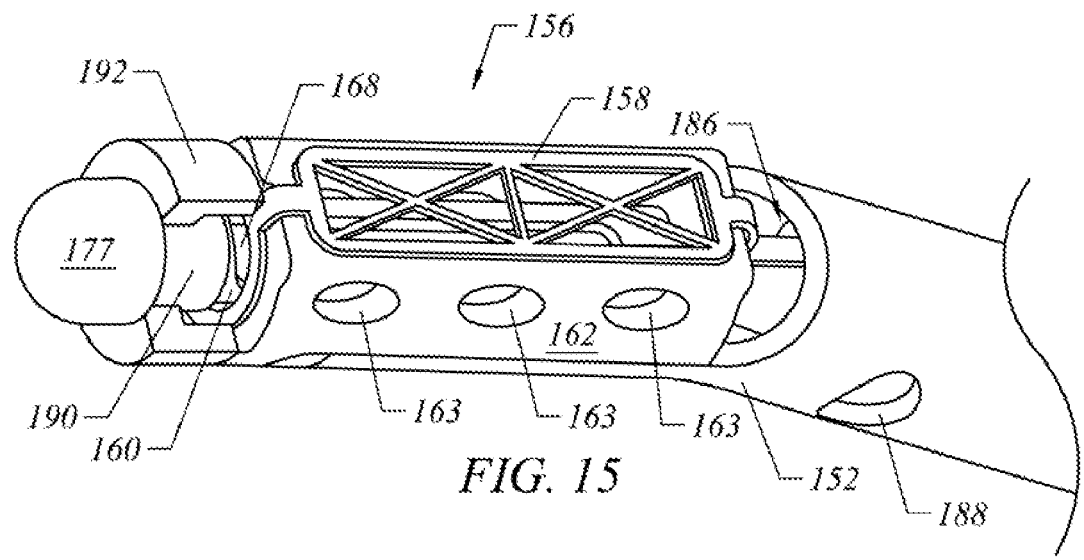
FIG. 15 shows an enlarged view of the distal end of an electrosurgical system, with portions removed, according to the present disclosure.
Figure 16:
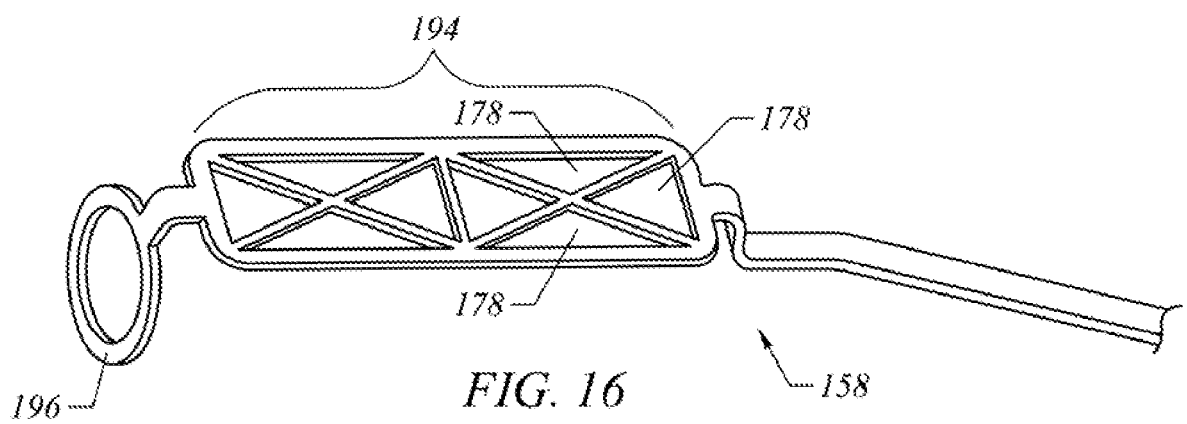
FIG. 16 shows an embodiment of an active electrode according to the present disclosure.

As shown in FIG. 16, active electrode (158) includes a screen or mesh portion (194) comprising a plurality of apertures (178). Active electrode (158) also includes a distal loop assembly (196). As shown in FIG. 15, loop assembly (196) is adapted to interface with distal end portion (156) of shaft (152). As shown, bushing (190) is disposed circumferentially around the exterior surface of return electrode (160). Note that in FIG. 15 a proximal portion of bushing (190) has been cut away to allow return electrode (160) and chamber (168) to be in view. In the present embodiment bushing (190) preferably extends slightly in a proximal direction such that loop section (196) may then be disposed around bushing (190) and such that bushing (190) insulates loop (196) from return electrode (160). A distal spacer (192), also shown in FIG. 15 with a portion removed, may be further provided circumferentially around bushing (190) to insulate cap (177) from active electrode (158). Distal spacer (192) and cap (177) may aid in blunt dissection and protect active electrode (158) during insertion into body structure 138. In an alternate embodiment active electrode (158) may be brazed onto distal end portion (156) of shaft (152). In an alternate embodiment electrode (158) may include a second loop located, for example, at the opposite end of screen (194) for interfacing with distal end portion (156).

As shown in FIGS. 13-15 an electric insulator or spacer element (162) is provided between active electrode (158) and return electrode (160). Insulator (162) includes an opening for allowing conductive fluid to flow between active electrode (158) and return electrode (160). Additionally, insulator (162) may include apertures (163) formed therein. Apertures (163) may be formed uniformly on the body of the insulator (162) or may be provided along only a portion of insulator (162). Apertures (163) may be elliptical (as shown), circular or have any other suitable shape. Apertures (162) may open into chamber (168) and/or onto a surface of return electrode (160).

In this manner apertures (163) may contribute to ensuring that the charge density on the surface of return electrode (160) is lower than the charge density on the surface of active electrode (158). Apertures (163) preferably provide an exit path for conductive fluid (172) in chamber (168) in the event that screen portion (194) of active electrode (158) becomes clogged.

By the present description and Figures it is to be understood that the terms used herein are descriptive rather than limiting, and that changes, modifications, and substitutions may be made without departing from the scope of the invention. Also it will be appreciated that although the present apparatus, system is described in the context electrosurgery on an intervertebral disc, the apparatus and its use is not restricted to treating discs but is applicable in general for electrosurgical procedures wherein is desired to minimize exposure of the tissue to electrical stimulation, and where access to the tissue is limited. Therefore the invention is not limited to the embodiments described herein, but is defined by the scope of the appended claims.

What is claimed is:

1. An electrosurgical apparatus comprising:
   a shaft having a proximal end portion and a distal end portion;
   an active electrode disposed on a surface of the distal end portion of the shaft;
   a return electrode disposed within the distal end portion of the shaft;
   wherein the shaft comprises a conductive cap disposed at a distal end of the shaft and in electrical communication with the return electrode and wherein the conductive cap is spaced sufficiently from the active electrode to minimize generation of an electric arc between the active electrode and the conductive cap;
   wherein the shaft comprises an insulating member positioned on the distal end portion of the shaft and preventing direct electrical contact between the active and return electrodes;
   electrical conductors adapted for applying a radio-frequency voltage difference across the active and return electrodes,
   wherein the active electrode and return electrode define a chamber within the distal end portion of the shaft such that the chamber is between the active electrode and the return electrode, the chamber allowing for electrical communication therein between the active electrode and the return electrode in the presence of an electrically conductive fluid; and
   wherein the shaft comprises an aspiration lumen having a plurality of inlet apertures formed along a selected length of the shaft.

2. The electrosurgical apparatus of claim 1 wherein the selected length is between about one centimeter and about five centimeters.

3. The electrosurgical apparatus of claim 1 wherein the selected length is between about two centimeters and about three centimeters.

4. The electrosurgical apparatus of claim 1 wherein the selected length of the shaft comprises a first portion for insertion within a target tissue structure and a second portion for venting outside of the target tissue structure.

5. The electrosurgical apparatus of claim 4 wherein the target tissue structure comprises an intervertebral disc.

6. The electrosurgical apparatus of claim 4 wherein the collective area of the apertures in the second portion of the selected length is at least equal to a cross sectional area of the aspiration lumen.

7. The electrosurgical apparatus of claim 1 wherein the aspiration lumen is in communication with a suction source.

8. The electrosurgical apparatus of claim 1 wherein the aspiration lumen and the plurality of apertures are adapted to allow fluid to flow away from the target tissue through one or more of the apertures without requiring a suction source.

9. The electrosurgical apparatus of claim 1 wherein the inlet apertures are substantially evenly spaced along the selected length of the shaft.

10. The electrosurgical apparatus of claim 1 wherein the inlet apertures are spaced along the circumference of the shaft.

11. The electrosurgical apparatus of claim 1 wherein the active electrode comprises a screen section having a plurality of apertures formed therein.

12. The electrosurgical apparatus of claim 11 wherein the active electrode comprises a distal assembly loop for interfacing with the distal end portion of the shaft.

13. The electrosurgical apparatus of claim 11 wherein the active electrode is brazed onto the distal end portion of the shaft.

14. The electrosurgical apparatus of claim 1 wherein the insulating member comprises a plurality of apertures formed therein.

15. An electrosurgical instrument for treating tissue within a body, comprising:
   a shaft having a proximal end portion and a distal end portion;
   an active electrode comprising a tissue-contacting surface on the distal end portion of the shaft;
   a return electrode recessed within the shaft; and
   wherein the shaft comprises a conductive cap disposed at a distal end of the shaft and in electrical communication with the return electrode and wherein the conductive cap is spaced sufficiently from the active electrode to minimize generation of an electric arc between the active electrode and the conductive cap;
   wherein the shaft comprises an insulator separating the active electrode and the return electrode, wherein the tissue-contacting surface is adapted for generating plasma upon application of a radio frequency voltage across the active and return electrode in the presence of an electrically conducting fluid; and
   wherein the shaft comprises an aspiration lumen having a plurality of inlet apertures formed along a selected length of the shaft, wherein the selected length of the shaft comprises a first portion for insertion within a target tissue structure and a second portion for venting outside of the target tissue structure.

16. The electrosurgical instrument of claim 15 wherein the selected length is between about one centimeter and about five centimeters.

17. A system for performing an electrosurgical procedure on a target tissue within a body structure using plasma, the system comprising:
   an electrosurgical instrument comprising a shaft;
   an electrically conductive fluid supply having a discharge port on a distal end portion the shaft; and
   a radio-frequency voltage supply connected to the electrosurgical instrument, wherein the electrosurgical instrument further comprises:
   an active electrode on the distal end portion;
   a return electrode recessed within the shaft;
   wherein the shaft comprises an electrical insulator separating the active and return electrode;
   wherein the shaft comprises a conductive cap disposed at a distal end of the shaft and in electrical communication with the return electrode and wherein the conductive cap is spaced sufficiently from the active electrode to minimize generation of an electric arc between the active electrode and the conductive cap; and
   wherein the shaft comprises an aspiration lumen having a plurality of inlet apertures formed along a selected length of the shaft, wherein the selected length of the shaft comprises a first portion for insertion within a target tissue structure and a second portion for venting outside of the target tissue structure.

18. The electrosurgical apparatus of claim 17 wherein the active electrode comprises a screen section having a plurality of apertures formed therein.

19. The electrosurgical apparatus of claim 17 wherein the active electrode comprises a distal assembly loop for interfacing with the distal end portion of the shaft.

* * * * *